(12) United States Patent
Noguchi

(10) Patent No.: US 12,115,022 B2
(45) Date of Patent: Oct. 15, 2024

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Masafumi Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 148 days.

(21) Appl. No.: 17/393,891

(22) Filed: Aug. 4, 2021

(65) Prior Publication Data

US 2021/0361261 A1 Nov. 25, 2021

Related U.S. Application Data

(63) Continuation of application No. PCT/JP2019/042934, filed on Oct. 31, 2019.

(30) Foreign Application Priority Data

Feb. 15, 2019 (JP) ................................. 2019-025967

(51) Int. Cl.
*A61B 8/00* (2006.01)
*A61B 8/08* (2006.01)

(52) U.S. Cl.
CPC ................ *A61B 8/462* (2013.01); *A61B 8/42* (2013.01); *A61B 8/467* (2013.01); *A61B 8/5292* (2013.01); *A61B 8/54* (2013.01)

(58) Field of Classification Search
CPC ........... A61B 8/462; A61B 8/42; A61B 8/467; A61B 8/5292; A61B 8/54; A61B 8/4245;
(Continued)

(56) References Cited

U.S. PATENT DOCUMENTS

| 2008/0208048 A1* | 8/2008 | Maruyama ................ A61B 8/06 600/437 |
| 2011/0245670 A1* | 10/2011 | Tashiro ................... A61B 8/466 600/443 |
| 2013/0268203 A1 | 10/2013 | Pyloth |

(Continued)

FOREIGN PATENT DOCUMENTS

| CN | 105653859 A | 6/2016 |
| CN | 108320798 A | 7/2018 |

(Continued)

OTHER PUBLICATIONS

The extended European search report issued by the European Patent Office on Mar. 11, 2022, which corresponds to European Patent Application No. 19915403.0-1126 and is related to U.S. Appl. No. 17/393,891.

(Continued)

*Primary Examiner* — Baisakhi Roy
*Assistant Examiner* — Kaitlyn E Sebastian
(74) *Attorney, Agent, or Firm* — Studebaker & Brackett PC

(57) ABSTRACT

An ultrasound diagnostic apparatus includes an ultrasound probe that performs transmission and reception of an ultrasonic wave to and from a subject, a head-mounted display having a camera unit configured to acquire a camera image obtained by imaging a field of view in front of a user and a display unit, a measurement spot decision unit that, in a case where subject information including at least one of a symptom or a disease of the subject is input, decides a measurement spot where the transmission and reception of the ultrasonic wave is desired, based on the spot subject information, and a navigation image generation unit that recognizes the subject from the camera image, generates a navigation image indicating a position of the measurement spot decided by the measurement spot decision unit with respect to the recognized subject, and displays the generated navi- (Continued)

gation image on the display unit of the head-mounted display.

19 Claims, 12 Drawing Sheets

(58) Field of Classification Search
CPC ... A61B 8/4472; A61B 8/4444; A61B 8/4483; A61B 8/4416; A61B 8/488; A61B 8/0841
See application file for complete search history.

(56) References Cited

U.S. PATENT DOCUMENTS

| | | | |
|---|---|---|---|
| 2015/0019246 A1* | 1/2015 | Inoue | G16H 50/20 705/2 |
| 2017/0360401 A1* | 12/2017 | Rothberg | G06V 30/194 |
| 2018/0225993 A1 | 8/2018 | Buras et al. | |

FOREIGN PATENT DOCUMENTS

| | | | | |
|---|---|---|---|---|
| CN | 109674533 B | * | 7/2022 | ............ A61B 34/20 |
| JP | 2011004951 A | * | 1/2011 | |
| JP | 2011-200533 A | | 10/2011 | |
| JP | 2011-206281 A | | 10/2011 | |
| JP | 2016-083021 A | | 5/2016 | |
| JP | 2016-83022 A | | 5/2016 | |
| WO | 2017/150484 A1 | | 9/2017 | |
| WO | 2017/222970 A1 | | 12/2017 | |

OTHER PUBLICATIONS

International Search Report issued in PCT/JP2019/042934; mailed Dec. 17, 2019.
International Preliminary Report On Patentability and Written Opinion issued in PCT/JP2019/042934; issued Aug. 10, 2021.
An Office Action mailed by China National Intellectual Property Administration on Oct. 13, 2023, which corresponds to Chinese Patent Application No. 201980092033.4 and is related to U.S. Appl. No. 17/393,891; with English language translation.
An Office Action mailed by China National Intellectual Property Administration on Apr. 10, 2024, which corresponds to Chinese Patent Application No. 201980092033.4 and is related to U.S. Appl. No. 17/393,891; with English language translation.

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

This application is a Continuation of PCT International Application No. PCT/JP2019/042934 filed on Oct. 31, 2019, which claims priority under 35 U.S.C. § 119(a) to Japanese Patent Application No. 2019-025967 filed on Feb. 15, 2019. Each of the above application(s) is hereby expressly incorporated by reference, in its entirety, into the present application.

BACKGROUND OF THE INVENTION

1. Field of the Invention

The present invention relates to an ultrasound diagnostic apparatus and a method of controlling an ultrasound diagnostic apparatus, and in particular, to an ultrasound diagnostic apparatus comprising a head-mounted display and a method of controlling an ultrasound diagnostic apparatus.

2. Description of the Related Art

Hitherto, in a medical field, an ultrasound diagnostic apparatus using an ultrasound image has come into practical use. In general, this kind of ultrasound diagnostic apparatus has an ultrasound probe that incorporates a transducer array. The ultrasound probe transmits ultrasonic waves toward a subject and receives ultrasound echoes from the subject, and reception signals are electrically processed to generate an ultrasound image.

In such an ultrasound diagnostic apparatus, usually, a monitor on which the ultrasound image is often disposed at a position away from the ultrasound probe, such as a bedside, and thus, a user needs to alternately move a line of sight between the ultrasound probe at hand and the monitor. To reduce the movement of the line of sight of the user, for example, an ultrasound diagnostic apparatus comprising a so-called head-mounted display as disclosed in JP2011-200533A has been developed. In the ultrasound diagnostic apparatus of JP2011-200533A, an ultrasound image is displayed on the head-mounted display.

SUMMARY OF THE INVENTION

Even though the user uses the ultrasound diagnostic apparatus disclosed in JP2011-200533A, there is a need to decide a measurement spot of the subject where the ultrasound probe is to be positioned, from a symptom or the like of the subject. To decide an appropriate measurement spot of the subject from the symptom or the like of the subject, exclusive knowledge and experience are needed. In particular, a user who has low proficiency has difficulty in deciding an appropriate measurement spot of the subject and performing ultrasonography on the subject.

The invention has been accomplished to solve the problem in the related art, and an object of the invention is to provide an ultrasound diagnostic apparatus and a method of controlling an ultrasound diagnostic apparatus capable of allowing a user to easily perform ultrasonography on a subject regardless of user's proficiency.

To achieve the above-described object, there is provided a first ultrasound diagnostic apparatus according to the invention comprising an ultrasound probe that is positioned at a measurement spot of a subject to perform transmission and reception of an ultrasonic wave to and from the subject, a head-mounted display that is mounted on a head of a user and has a camera unit configured to acquire a camera image obtained by imaging a field of view in front of the user and a display unit, a measurement spot decision unit that, in a case where subject information including at least one of a symptom or a disease of the subject is input, decides at least one measurement spot where the transmission and reception of the ultrasonic wave by the ultrasound probe is desired, based on the input subject information, and a navigation image generation unit that recognizes the subject from the camera image acquired by the camera unit of the head-mounted display, generates a navigation image indicating a position of the measurement spot decided by the measurement spot decision unit with respect to the recognized subject, and displays the generated navigation image on the display unit of the head-mounted display.

It is preferable that the subject information further includes at least one of a medical history, a status of treatment, a health status, or information regarding a body of the subject.

The measurement spot decision unit may estimate a part in the subject related to at least one of the symptom or the disease of the subject from the subject information and a status of the part, and may decide the at least one measurement spot based on the estimated part in the subject and the estimated status of the part.

In this case, the navigation image generation unit may include information representing the part in the subject and the status of the part used for the decision of the measurement spot by the measurement spot decision unit, in the navigation image.

The ultrasound diagnostic apparatus may further comprise a measurement procedure association unit that associates a given measurement procedure with the part in the subject and the status of the part estimated by the measurement spot decision unit, and the navigation image generation unit may include information representing the measurement procedure associated by the measurement procedure association unit, in the navigation image.

In a case where a plurality of symptoms are input as the subject information and a plurality of candidates of the measurement spot are derived, the measurement spot decision unit may decide the at least one measurement spot by giving a higher evaluation value to the plurality of candidates of the measurement spot as the number of related symptoms is greater and narrowing down the plurality of candidates based on the evaluation values.

The ultrasound diagnostic apparatus may further comprise a ground derivation unit that derives a description to be a ground for the decision of the measurement spot by the measurement spot decision unit, from the subject information, and the navigation image generation unit may include information representing the description to be the ground derived by the ground derivation unit, in the navigation image.

The ultrasound diagnostic apparatus may further comprise a probe detection unit that detects the ultrasound probe from the camera image acquired by the camera unit of the head-mounted display, and a position determination unit that determines whether or not a position of the ultrasound probe detected by the probe detection unit overlaps the position of the measurement spot indicated by the navigation image generated by the navigation image generation unit.

It is preferable that the ultrasound diagnostic apparatus further comprises a transmission and reception controller that controls the transmission and reception of the ultrasound wave by the ultrasound probe in a given observation mode and under a given transmission and reception condition.

In this case, in a case where the position determination unit determines that the position of the ultrasound probe overlaps the position of the measurement spot, the transmission and reception controller may control the transmission and reception of the ultrasonic wave by the ultrasound probe under a transmission and reception condition corresponding to the measurement spot where the ultrasound probe is positioned.

In a case where the position determination unit determines that the position of the ultrasound probe overlaps the position of the measurement spot, the transmission and reception controller may control the transmission and reception of the ultrasonic wave by the ultrasound probe in an observation mode corresponding to the measurement spot where the ultrasound probe is positioned.

The ultrasound diagnostic apparatus may further comprise an ultrasound image generation unit that generates an ultrasound image based on a reception signal acquired through the transmission and reception of the ultrasonic wave to and from the subject by the ultrasound probe, and a part recognition unit that, in a case where the position determination unit determines that the position of the ultrasound probe overlaps the position of the measurement spot, recognizes a part in the subject from the ultrasound image generated by the ultrasound image generation unit, and the transmission and reception controller may control the transmission and reception of the ultrasonic wave by the ultrasound probe under a transmission and reception condition corresponding to the part in the subject recognized by the part recognition unit.

In this case, the ultrasound diagnostic apparatus may further comprise a measurement unit that, in a case where the part in the subject is recognized by the part recognition unit, performs measurement regarding the part recognized by the part recognition unit based on the ultrasound image generated by the ultrasound image generation unit under a measurement condition corresponding to the part in the subject recognized by the part recognition unit.

In a case where a plurality of the measurement spots are decided by the measurement spot decision unit, the navigation image generation unit may generate the navigation image in which the measurement spot closest to the position of the ultrasound probe detected by the probe detection unit among the plurality of measurement spots is highlighted.

The measurement spot decision unit may estimate a plurality of parts in the subject and statuses of the plurality of parts based on the subject information, and may decide a plurality of the measurement spots based on the plurality of estimated parts in the subject and the estimated statuses of the plurality of parts, and the navigation image generation unit may include only information representing the part in the subject related to the measurement spot closest to the position of the ultrasound probe detected by the probe detection unit and the status of the part among the parts in the subject related to the plurality of measurement spots and the statuses of the parts, in the navigation image.

The ultrasound diagnostic apparatus may further comprise a probe detection unit that detects the ultrasound probe from the camera image captured by the camera unit of the head-mounted display, a position determination unit that determines whether or not a position of the ultrasound probe detected by the probe detection unit overlaps the position of the measurement spot indicated by the navigation image generated by the navigation image generation unit, and a transmission and reception controller that controls the transmission and reception of the ultrasonic wave by the ultrasound probe in a given observation mode and under a given transmission and reception condition, and in a case where the position determination unit determines that the position of the ultrasound probe overlaps the position of the measurement spot, the transmission and reception controller may control the transmission and reception of the ultrasonic wave by the ultrasound probe in an observation mode and under a transmission and reception condition based on the measurement procedure associated with the part in the subject related to the measurement spot where the ultrasound probe is positioned and the status of the part by the measurement procedure association unit.

The measurement spot decision unit may estimate a plurality of parts in the subject and statuses of the plurality of parts based on the subject information, may decide the measurement spot based on the plurality of estimated parts in the subject and the estimated statuses of the plurality of parts, and may store a given degree of urgency with respect to each of a plurality of estimatable parts in the subject and statuses of the plurality of parts, and the navigation image generation unit may include information representing the degree of urgency of a part in the subject and a status of the part related to the measurement spot, in the navigation image.

In this case, the measurement spot decision unit may decide a plurality of the measurement spots based on the plurality of estimated parts in the subject and the estimated statuses of the plurality of parts, and may give priority to the plurality of measurement spots based on the degree of urgency of the plurality of estimated parts in the subject, and the navigation image generation unit may generate the navigation image with the plurality of measurement spots given the priority.

The ultrasound diagnostic apparatus may further comprise an input device that is provided for the user to perform an input operation, and the subject information is input by the user through the input device.

A method of controlling an ultrasound diagnostic apparatus according to the invention comprises acquiring a camera image obtained by imaging a subject with a camera unit of a head-mounted display mounted on a head of a user, in a case where subject information including at least one of a symptom or a disease of the subject is input, deciding a measurement spot where transmission and reception of an ultrasonic wave by an ultrasound probe is desired, based on the input subject information, recognizing the subject from the acquired camera image and generating a navigation image indicating a position of the measurement spot with respect to the recognized subject, and displaying the generated navigation image on a display unit of the head-mounted display.

A second ultrasound diagnostic apparatus according to the invention comprises an ultrasound probe that is positioned at a measurement spot of a subject to perform transmission and reception of an ultrasonic wave to and from the subject, a head-mounted display that is mounted on a head of a user and has a camera unit configured to acquire a camera image obtained by imaging a field of view in front of the user and a display unit, and a processor that, in a case where subject information including at least one of a symptom or a disease of the subject is input, decides at least one measurement spot where the transmission and reception of the ultrasonic wave by the ultrasound probe is desired, based on the input subject information, recognizes the subject from the camera image acquired by the camera unit of the head-mounted display, generates a navigation image indicating a position of the decided measurement spot with respect to the recognized subject, and displays the generated navigation image on the display unit of the head-mounted display.

According to the invention, the ultrasound diagnostic apparatus comprises the head-mounted display that is mounted on the head of the user and has the camera unit configured to acquire the camera image obtained by imaging the field of view in front of the user and the display unit, the measurement spot decision unit that, in a case where the subject information including at least one of the symptom and the disease of the subject is input, decides at least one measurement spot where the transmission and reception of the ultrasonic wave by the ultrasound probe is desired, based on the input subject information, and the navigation image generation unit recognizes the subject from the camera image acquired by the camera unit of the head-mounted display, generates the navigation image indicating the position of the measurement spot decided by the measurement spot decision unit with respect to the recognized subject, and displays the generated navigation image on the display unit of the head-mounted display. Therefore, it is possible to allow the user to easily perform ultrasonography on the subject regardless of user's proficiency.

DESCRIPTION OF THE PREFERRED EMBODIMENTS

Hereinafter, embodiments of the invention will be described referring to the accompanying drawings.

The description of components described below is provided based on a representative embodiment of the invention, but the invention is not limited to such an embodiment.

Embodiment 1

Figure 1:
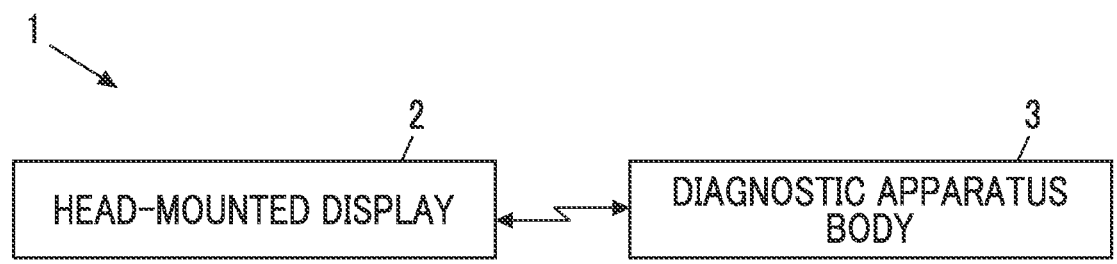
FIG. 1 is a block diagram showing the configuration of an ultrasound diagnostic apparatus according to Embodiment 1 of the invention.

FIG. 1 shows the configuration of an ultrasound diagnostic apparatus 1 according to Embodiment 1 of the invention. The ultrasound diagnostic apparatus 1 comprises a head-mounted display 2 and a diagnostic apparatus body 3, and the head-mounted display 2 and the diagnostic apparatus body 3 are connected in a wireless state.

Figure 2:
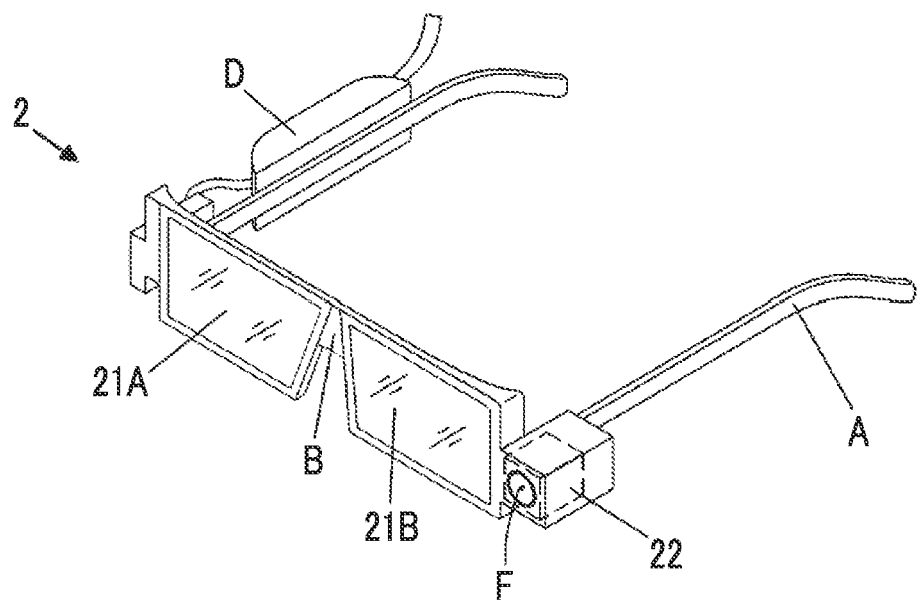
FIG. 2 is a diagram showing an example of a head-mounted display in Embodiment 1 of the invention.

The head-mounted display 2 is a display device that is mounted on the head of the user and is viewed by the user who mounts the head-mounted display 2, and as shown in FIG. 2, has a shape of so-called spectacles. The head-mounted display 2 comprises two display units 21A and 21B, and the two display units 21A and 21B are connected by a bridge portion B, and temple portions A are connected to end portions of the two display units 21A and 21B, respectively. For example, the bridge portion B is placed and fixed on a nose of the user, and the two temple portions A are placed and fixed on both ears of the user, whereby the head-mounted display 2 is fixed to the head of the subject. In this case, the two display units 21A and 21B face right and left eyes of the user, respectively.

A camera unit 22 that has an imaging lens F disposed on a front surface is attached to a connection portion of the left display unit 21B and the temple portion A as viewed from the user who mounts the head-mounted display 2. An accommodation portion D where various circuits necessary for the operation of the head-mounted display 2, a battery, and the like are accommodated is disposed in the temple portion A connected to the right display unit 21A.

Figure 3:
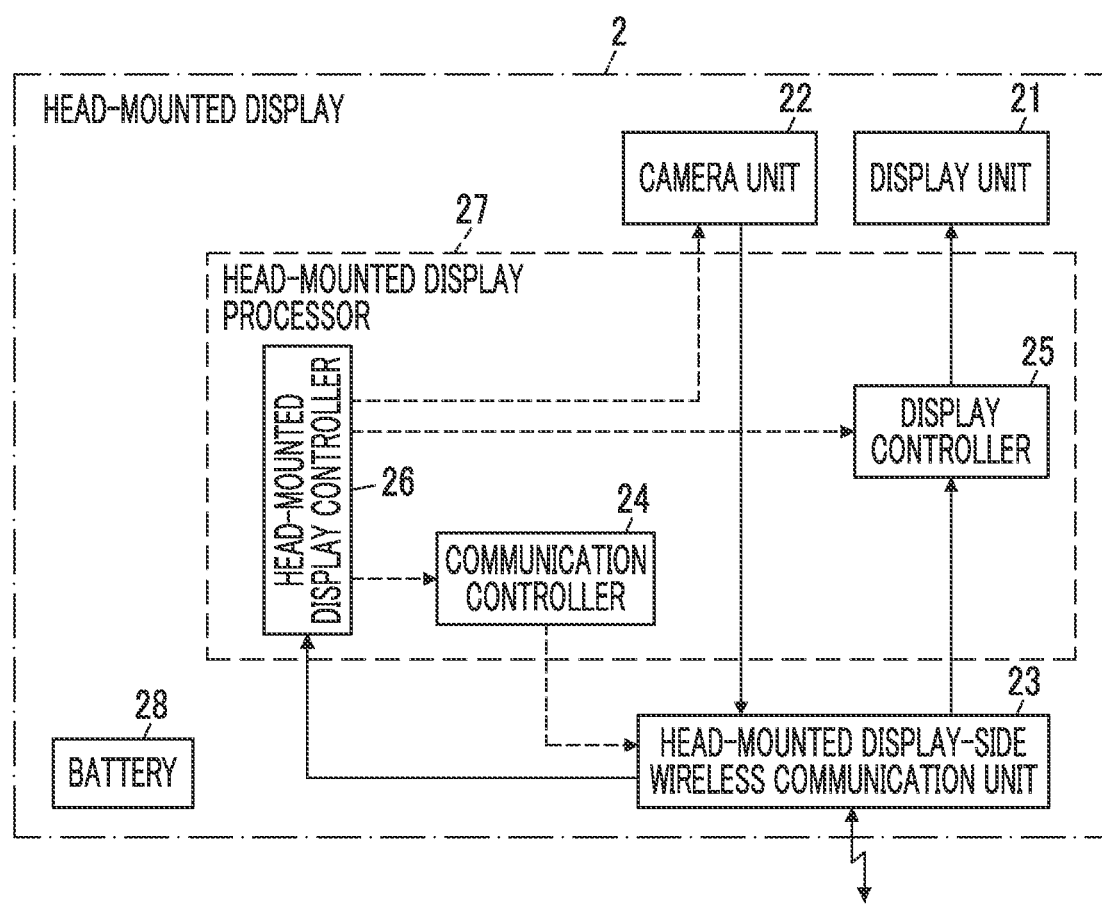
FIG. 3 is a block diagram showing the configuration of the head-mounted display in Embodiment 1 of the invention.

FIG. 3 shows the configuration of the head-mounted display 2. The head-mounted display 2 has a head-mounted display-side wireless communication unit 23, and the camera unit 22, a communication controller 24, and a display controller 25 are connected to the head-mounted display-side wireless communication remit 23. A display unit 21 is connected to the display controller 25. A head-mounted display controller 26 is connected to the camera unit 22, the head-mounted display-side wireless communication unit 23, the communication controller 24, and the display controller 25.

For description, the two display units 21A and 21B in FIG. 2 are collectively referred to as the display unit 21.

The communication controller 24, the display controller 25, and the head-mounted display controller 26 configure a head-mounted display processor 27. A battery 28 is incorporated in the head-mounted display 2. The head-mounted display-side wireless communication unit 23, the head-mounted display processor 27, and the battery 28 are accommodated in the accommodation portion D of the head-mounted display 2.

The camera unit 22 of the head-mounted display 2 generates a camera image obtained by imaging a field of view in front of the user through the imaging lens F. Though not shown, the camera unit 22 incorporates an image sensor that images the field of view in front of the user through the imaging lens F to acquire a camera image signal as an analog signal, an analog signal processing circuit that amplifies the camera image signal acquired by the image sensor to convert the camera image signal to a digital signal, and a digital signal processing circuit that performs various kinds of correction, such as gain correction, on the converted digital signal to generate a camera image.

The analog signal processing circuit and the digital signal processing circuit can also be incorporated in the head-mounted display processor 27.

The head-mounted display-side wireless communication unit 23 of the head-mounted display 2 includes an antenna that performs transmission and reception of radio waves, and transmits the camera image generated by the camera unit 22 to the diagnostic apparatus body 3. In this case, for example, the head-mounted display-side wireless communication unit 23 modulates a carrier based on the camera image to generate a transmission signal representing the camera image and supplies the generated transmission signal to the antenna, and transmits the radio waves from the antenna, thereby transmitting the camera image to the diagnostic apparatus body 3 in a wireless manner. As a modulation system of the carrier, for example, amplitude shift keying (ASK), phase shift keying (PSK), quadrature phase shift keying (QPSK), or 16 quadrature amplitude modulation (16QAM) is used. The head-mounted display-side wireless communication unit 23 receives data, such as an ultrasound image transmitted from the diagnostic apparatus body 3, and transmits the received data to the display unit 21 through the display controller 25. The head-mounted display-side wireless communication unit 23 receives instruction information and the like for instructing the operation of the head-mounted display 2 from the diagnostic apparatus body 3 and outputs the received instruction information and the like to the head-mounted display controller 26.

The display unit 21 of the head-mounted display 2 has transmittance to secure the field of view of the user in a state in which the user mounts the head-mounted display 2. The display unit 21 is a display that displays data, such as an ultrasound image transmitted from the diagnostic apparatus body 3.

The display controller 25 of the head-mounted display processor 27 executes predetermined processing on data and the like transmitted from the diagnostic apparatus body 3 and displays the ultrasound image and the like on the display unit 21 under the control of the head-mounted display controller 26.

The communication controller 24 of the head-mounted display processor 27 performs control such that the head-mounted display-side wireless communication unit 23 transmits the camera image and receives the ultrasound image and the like with transmission and reception field intensity set by the head-mounted display controller 26.

The head-mounted display controller 26 of the head-mounted display processor 27 performs control of each unit of the head-mounted display 2 based on a program stored in advance, and the instruction information and the like transmitted from the diagnostic apparatus body 3 in a wireless manner.

The battery 28 of the head-mounted display 2 is incorporated in the head-mounted display 2, and supplies electric power to each circuit of the head-mounted display 2.

Although the head-mounted display processor 27 having the communication controller 24, the display controller 25, and the head-mounted display controller 26 is configured with a central processing unit (CPU) and a control program causing the CPU to execute various kinds of processing, the head-mounted display processor 27 may be configured using a field programmable gate array (FPGA), a digital signal processor (DSP), an application specific integrated circuit (ASIC), a graphics processing unit (GPU), or other integrated circuits (ICs) or may be configured by combining the ICs. The communication controller 24, the display controller 25, and the head-mounted display controller 26 can also be configured to be partially or wholly integrated into one CPU or the like.

Figure 4:
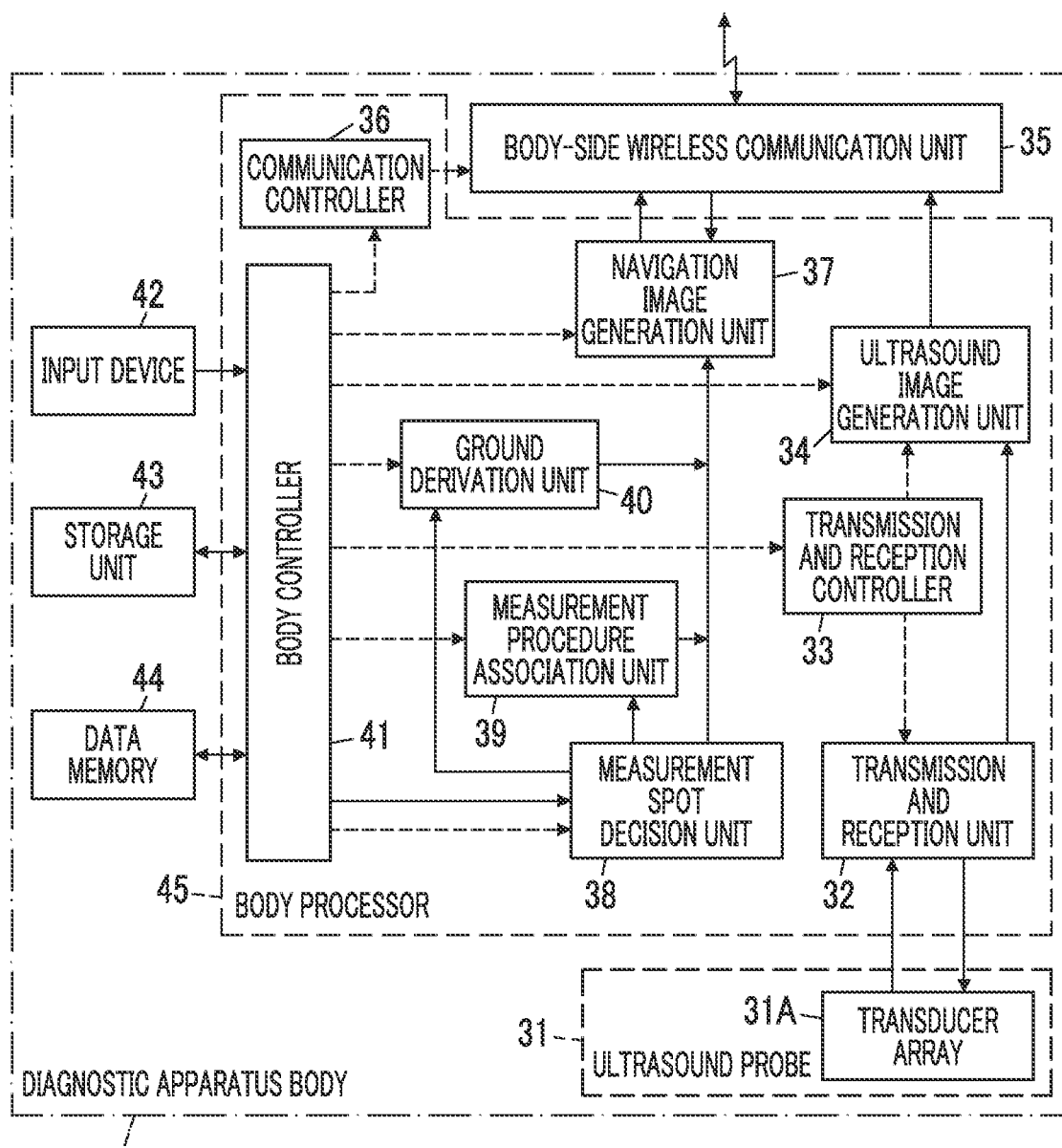
FIG. 4 is a block diagram showing the configuration of a diagnostic apparatus body in Embodiment 1 of the invention.

As shown in FIG. 4, the diagnostic apparatus body 3 comprises an ultrasound probe 31 having a transducer array 31A, and a transmission and reception unit 32 is connected to the transducer array 31A. A transmission and reception controller 33 and an ultrasound image generation unit 34 are connected to the transmission and reception unit 32, and a body-side wireless communication unit 35 is connected to the ultrasound image generation unit 34. A communication controller 36 and a navigation image generation unit 37 are connected to the body-side wireless communication unit 35. A measurement spot decision unit 38, a measurement procedure association unit 39, and a ground derivation unit 40 are connected to the navigation image generation unit 37. The measurement procedure association unit 39 and the ground derivation unit 40 are connected to the measurement spot decision unit 38.

A body controller 41 is connected to the transmission and reception controller 33, the ultrasound image generation unit 34, the communication controller 36, the navigation image generation unit 37, the measurement spot decision unit 38, the measurement procedure association unit 39, and the ground derivation unit 40. An input device 42, a storage unit 43, and a data memory 44 are connected to the body controller 41. The body controller 41 and the storage unit 43, and the body controller 41 and the data memory 44 are connected to transfer information in two directions.

The transmission and reception unit 32, the transmission and reception controller 33, the ultrasound image generation unit 34, the communication controller 36, the navigation image generation unit 37, the measurement spot decision unit 38, the measurement procedure association unit 39, the ground derivation unit 40, and the body controller 41 configure a body processor 45.

The transducer array 31A of the ultrasound probe 31 has a plurality of transducers arranged in a one-dimensional or two-dimensional manner. Each transducer transmits an ultrasonic wave in response to a drive signal supplied from the transmission and reception unit 32, receives an ultrasound echo from a subject, and outputs a signal based on the ultrasound echo. Each transducer is configured by forming electrodes at both ends of a piezoelectric body made of, for example, piezoelectric ceramic represented by lead zirconatetitanate (PZT), a polymer piezoelectric element represented by poly vinylidene di fluoride (PVDF), piezoelectric single crystal represented by lead magnesium niobate-lead titanate (PMN-PT), or the like.

The transmission and reception controller 33 of the body processor 45 controls transmission and reception of ultrasonic waves by the transducer array 31A of the ultrasound probe 31 in a given observation mode and under a given transmission and reception condition. Here, the observation mode indicates a mode for generating a so-called B mode (Brightness mode) image, a mode for generating a Doppler image, and the like. The transmission and reception condition includes a gain of a signal in the transmission and reception unit 32, a dynamic range, a transmission focus position of an ultrasonic wave in the ultrasound image generation unit 34, a reception focus position, a display depth of an ultrasound image, and the like described below.

Figure 5:
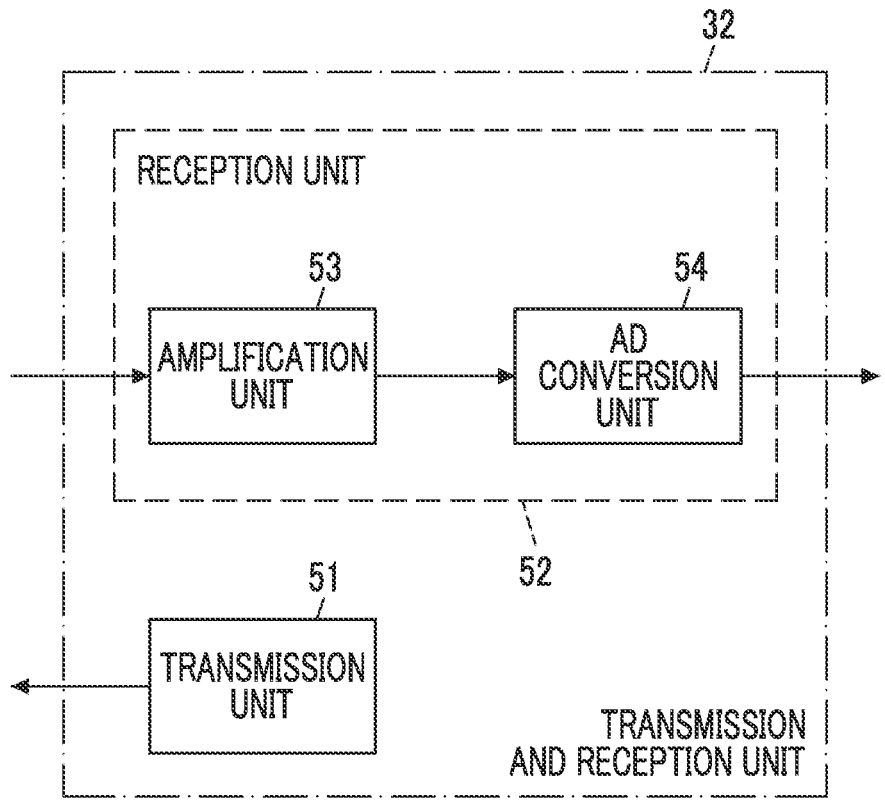
FIG. 5 is a block diagram showing the configuration of a transmission and reception unit in Embodiment 1 of the invention.

The transmission and reception unit 32 of the body processor 45 makes the transducer array 31A perform transmission and reception of ultrasonic waves under the control of the transmission and reception controller 33. As shown in FIG. 5, the transmission and reception unit 32 is configured with a transmission unit 51 and a reception unit 52.

The transmission unit 51 of the transmission and reception unit 32 includes, for example, a plurality of pulse generators, and adjusts a delay amount of each drive signal based on a transmission delay pattern selected in response to a control signal from the transmission and reception controller 33 such that the ultrasonic waves transmitted from a plurality of transducers of the transducer array 31A form an ultrasonic beam, and supplies the drive signals to a plurality of transducers. In this way, in a case where a pulsed or continuous-wave voltage is applied to the electrodes of each of a plurality of transducers of the transducer array 31A, the piezoelectric body expands and contracts, and a pulsed or continuous-wave ultrasonic wave is generated from each of the transducers. An ultrasonic beam is formed from a combined wave of the ultrasonic waves.

The transmitted ultrasonic beam is reflected by, for example, a target, such as a part of the subject, and propagates toward the transducer array 31A of the ultrasound probe 31. The ultrasonic wave propagating toward the transducer array 31A is received by each transducer configuring the transducer array 31A. In this case, each transducer configuring the transducer array 31A expands and contracts with reception of the propagating ultrasound echo to generate an electrical signal, and outputs the electrical signal to the reception unit 52.

The reception unit 52 of the transmission and reception unit 32 executes processing of the signal output from the transducer array 31A in response to a control signal from the transmission and reception controller 33. As shown in FIG. 5, the reception unit 52 has an amplification unit 53 and an analog-digital (AD) conversion unit 54.

The amplification unit 53 amplifies the signal input from each transducer configuring the transducer array 31A and transmits the amplified signal to the AD conversion unit 54. The AD conversion unit 54 converts the signal transmitted from the amplification unit 53 into digital data, and transmits the converted data to the ultrasound image generation unit 34. In this case, for example, the amplification unit 53 amplifies the signal with a given gain, and the AD conversion unit 54 converts the signal into digital data with a given dynamic range.

Figure 6:
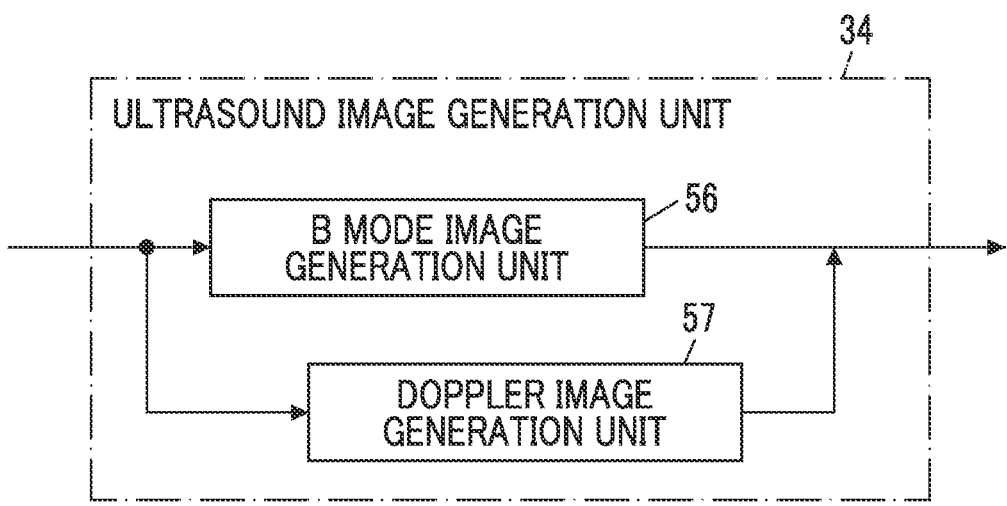
FIG. 6 is a block diagram showing the configuration of an ultrasound image generation unit in Embodiment 1 of the invention.

The ultrasound image generation unit 34 of the body processor 45 generates various ultrasound images based on the signal transmitted from the transmission and reception unit 32. As shown in FIG. 6, the ultrasound image generation unit 34 includes a B mode image generation unit 56 and a Doppler image generation unit 57.

The B mode image generation unit 56 executes so-called reception focus processing by giving a delay to each piece of data converted by the AD conversion unit 54 in compliance with a sound speed or a distribution of the sound speed set based on a reception delay pattern selected in response to a control signal from the transmission and reception controller 33 and performing additions. With the reception focus processing, each piece of data converted by the AD conversion unit 54 is subjected to phasing addition, and a sound ray signal with a narrowed focus of the ultrasound echo is acquired. The B mode image generation unit 56 performs correction of attenuation due to a propagation distance depending on a depth of a reflection position of the ultrasonic wave on the acquired sound ray signal, and then, executes envelope detection processing to generate a B mode image that is tomographic image information regarding a tissue in the subject. The B mode image generation unit 56 converts (raster-converts) the generated B mode image to an image compliant with a normal television signal scanning system, executes various kinds of necessary image processing, such as gradation processing, on the converted B mode image, and then, sends the B mode image to the body-side wireless communication unit 35.

The Doppler image generation unit 57 generates a Doppler image using a color Doppler method, for example. The Doppler image generation unit 57 performs frequency analysis on data converted by the AD conversion unit 54 to calculate a Doppler shift frequency and acquires information regarding a movement speed of a tissue in the subject as Doppler data. The Doppler image generation unit 57 converts each piece of Doppler data of each tissue in the subject into color information corresponding to the movement speed of the tissue and performs raster-conversion into an image compliant with a normal television signal scanning system, thereby generating a so-called color Doppler image (Doppler image). The Doppler image generation unit 57 executes various kinds of necessary image processing, such as gradation processing, on the generated Doppler image and superimposes the Doppler image on which the image processing is executed, on the corresponding B mode image.

The body-side wireless communication unit 35 of the diagnostic apparatus body 3 includes an antenna that performs transmission and reception of radio waves, and modulates a carrier based on the ultrasound image generated in the ultrasound image generation unit 34 to generate a transmission signal representing the ultrasound image. The body-side wireless communication unit 35 supplies the transmission signal representing the ultrasound image generated in this manner to the antenna and transmits the radio waves from the antenna, thereby sequentially transmitting the ultrasound images to the head-mounted display 2 in a wireless manner. As a modulation system of the carrier, ASK, PSK, QPSK, 16QAM, or the like is used. The body-side wireless communication unit 35 receives the camera image from the head-mounted display 2.

The communication controller 36 of the body processor 45 performs control such that the body-side wireless communication unit 35 performs transmission and reception of various kinds of data with transmission field intensity and reception field intensity set by the body controller 41.

The input device 42 of the diagnostic apparatus body 3 is provided for the user to perform an input operation, and can comprise a keyboard, a mouse, a trackball, a touch pad, a touch panel, a microphone, and the like.

The data memory 44 is a memory that stores subject information as information regarding the subject on which ultrasonography is to be performed and data regarding ultrasonography, such as a result of ultrasonography on the subject. For example, data regarding ultrasonography can be saved in the data memory 44 by an input operation of the user through the input device 42. For example, data regarding ultrasonography can be extracted from the data memory 44 by an input operation of the user through the input device 42. As the data memory 44, a recording medium, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

In a case where subject information including at least one of a symptom or a disease of the subject is input by the user through the input device 42 or the like, the measurement spot decision unit 38 of the body processor 45 decides a measurement spot of the subject where transmission and reception of the ultrasonic wave by the ultrasound probe 31 is desired, that is, a measurement spot of the subject where the ultrasound probe 31 should be positioned at the time of ultrasonography, based on the input subject information. The measurement spot decision unit 38 sends information regarding the decided measurement spot to the navigation image generation unit 37.

Here, the subject information that is input by the user through the input device 42 can include at least one of a medical history of the subject, a status of treatment of the subject, such as follow-up and a status of adverse reaction of ingestion, a health status of the subject, such as whether or not the subject is confined to a bed and a risk factor by a blood test, or physical information, such as the sex, age, and weight of the subject, in addition to at least one of the symptom or the disease of the subject.

Such subject information can be input, for example, text data, voice data, or the like input by the user through the input device 42. For example, the subject information can also be input by the user selecting a previous diagnostic result and the like of the subject stored in the data memory 44 through the input device 42.

In deciding the measurement spot of the subject, the measurement spot decision unit 38 first estimates a part in the subject related to at least one of the symptom or the disease of the subject and a status of the part based on the input subject information, and decides the measurement spot of the subject based on the estimated part in the subject and the estimated status of the part. The status of the part estimated by the measurement spot decision unit 38 corresponds to a viewpoint in deciding the measurement spot of the subject, and includes, for example, a disease name of the estimated part, a status of the estimated part, such as bleeding, and a size and a shape of the estimated part.

Here, the measurement spot decision unit 38 stores, for example, a measurement spot correspondence table in which a symptom of the subject, a part in the subject, a status of the part in the subject, and candidates of a measurement spot of the subject correspond to one another. The measurement spot correspondence table may be stored at another place in the diagnostic apparatus body 3. Referring to the measurement spot correspondence table, the part in the subject and the status of the part can be estimated from the symptom or the disease of the subject to decide the measurement spot of the subject. For example, in a case where a symptom "dull pain in right side" is included in the input subject information, the measurement spot decision unit 38 can estimate "right kidney" as a part in the subject related to "dull pain in right side" with reference to the measurement spot correspondence table and can estimate a disease name "renal calculus" as a status of "right kidney". The measurement spot decision unit 38 can decide "right side" as a measurement spot of the subject based on information of estimated "right kidney" and "renal calculus" with reference to the measurement spot correspondence table.

In the measurement spot correspondence table, for example, in addition to corresponding the symptom of the subject, the part in the subject, the status of the part in the subject, and the candidates of the measurement spot of the subject to one another, a medical history, a status of treatment, a health status, and physical information of the subject as information included in the subject information can also correspond to one another. With this, the measurement spot decision unit 38 can estimate a more appropriate part in the subject and a status of the part and can decide a more appropriate measurement spot with respect to the symptom or the disease of the subject.

In a case where there is a given measurement procedure with respect to the part in the subject and the status of the part estimated by the measurement spot decision unit 38 based on the subject information, the measurement procedure association unit 39 of the body processor 45 sends the measurement procedure to the navigation image generation unit 37 in association with the estimated part in the subject and the estimated status of the part. For example, the measurement procedure association unit 39 stores a measurement procedure association table in which given measurement procedures are associated with a plurality of parts in the subject estimatable by the measurement spot decision unit 38 and statuses of a plurality of parts, and can associate a measurement procedure with a part in the subject and a status of the part referring to the measurement procedure association table. For example, in a case where a symptom "dull pain in right side" is included in the input subject information, "right kidney" is estimated as a part in the subject by the measurement spot decision unit 38, and "renal calculus" is estimated as a status of "right kidney" by the measurement spot decision unit 38, a measurement procedure that "a color Doppler image is acquired after a B mode image is acquired" can be associated with a combination of "right kidney" and "renal calculus".

The ground derivation unit 40 of the body processor 45 derives a description to be a ground for the decision of the measurement spot of the subject by the measurement spot decision unit 38 from the subject information received through the measurement spot decision unit 38 and sends the derived description to be the ground to the navigation image generation unit 37. Here, the description to be the ground for the decision of the measurement spot includes, for example, symptoms, such as pain, discomfort, vomiting, eruption, swelling, and bleeding, diseases, such as cancer, tumor, inflammation, heart disease, calculus, and complication, a status of treatment, such as follow-up, post-operative confirmation, adverse reaction of ingestion, and recrudescence of symptoms, a possibility of a uterine disease in a case of female, description regarding physical information of the subject, such as a disease easily caused by aging and a disease easily caused by obesity, symptoms due to being confined to a bed, symptoms due to failure to dietary restriction, symptoms caused by fatigue, onset of a disease estimated by a risk factor from a blood test, and a possibility of internal bleeding by a traffic accident.

The ground derivation unit 40 can derive the description to be the ground for the decision of the measurement spot by extracting a keyword related to the measurement spot decided by the measurement spot decision unit 38, and the estimated part in the subject and the estimated status of the part from the subject information input by the user through the input device 42, for example. The ground derivation unit 40 can also derive the description to be the ground for the decision of the measurement spot by an inference based on the extracted keyword, for example.

Figure 7:
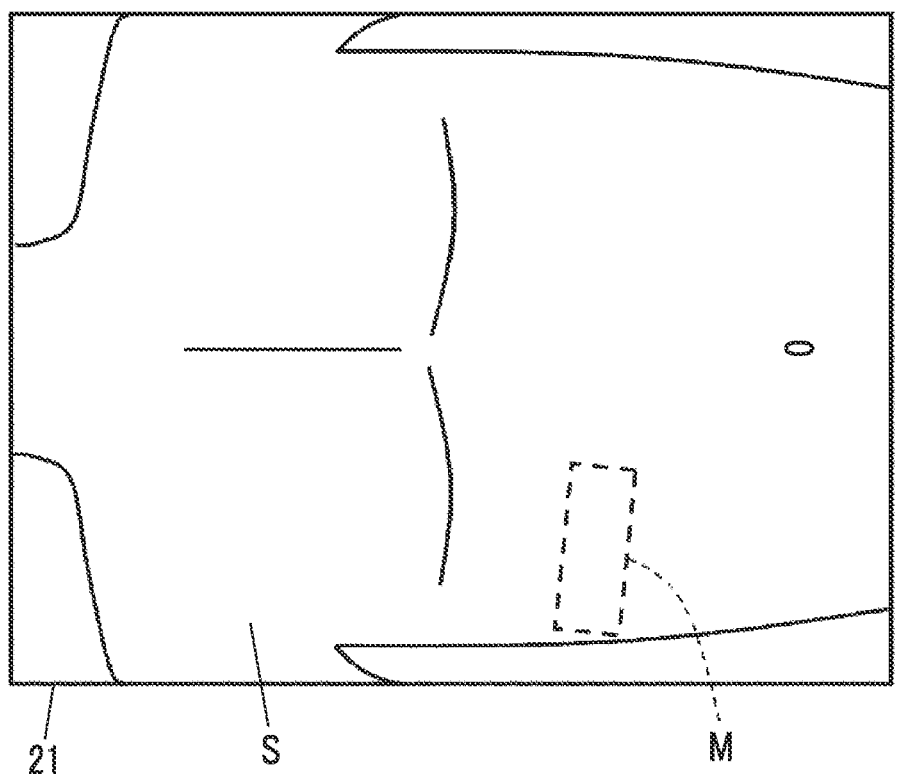
FIG. 7 is a diagram showing an example of a navigation image that includes a measurement spot mark indicating a measurement spot of a subject in Embodiment 1 of the invention.

The navigation image generation unit 37 of the body processor 45 recognizes the subject shown in the camera image received from the head-mounted display 2 through the body-side wireless communication unit 35 and generates a navigation image indicating a position of the measurement spot decided by the measurement spot decision unit 38 with respect to the recognized subject. The navigation image generation unit 37 transmits the generated navigation image to the head-mounted display 2 through the body-side wireless communication unit 35 and displays the navigation image on the display unit 21 of the head-mounted display 2. In FIG. 7, a measurement spot mark M that is positioned in the right side as the measurement spot of the subject S and is represented by a rectangularly closed broken line is shown as an example of a navigation image. The rectangularly closed broken line representing the measurement spot mark M represents a position and a direction of the ultrasound probe 31 that should be brought into contact with the measurement spot. In the example shown in FIG. 7, the user views the subject S through the transmissive display unit 21 of the head-mounted display 2, and the measurement spot mark M is displayed on the display unit 21 to overlap the right side of the subject S viewed by the user.

Figure 8:
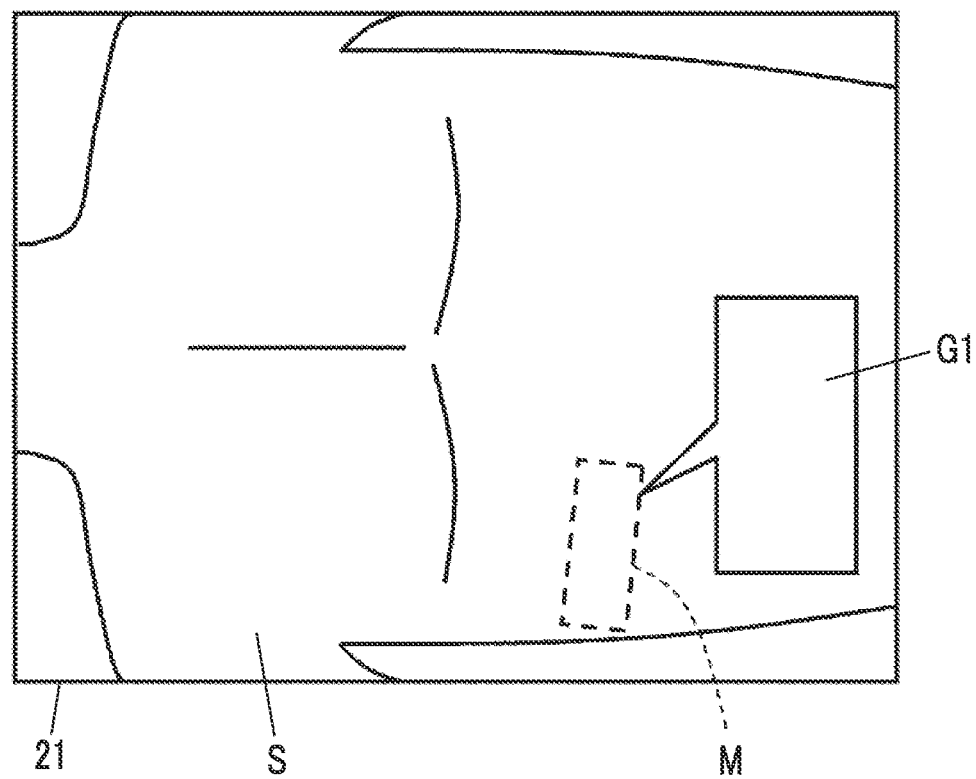
FIG. 8 is a diagram showing an example of a navigation image that includes a guide panel in Embodiment 1 of the invention.

The navigation image generation unit 37 can include, in the navigation image, the part of the subject and the status of the part used in the decision of the measurement spot by the measurement spot decision unit 38, information representing the measurement procedure associated with the part in the subject S and the status of the part by the measurement procedure association unit 39, and information representing the description of the ground derived by the ground derivation unit 40. For example, as shown in FIG. 8, the navigation image generation unit 37 can include, in the guide panel G1, the measurement spot mark M and a guide panel G1 connected to the measurement spot mark M in the navigation image, and can include text data representing a name of the part in the subject, text data representing the status of the part in the subject, text data (not shown) representing the measurement procedure, and text data (not shown) representing the description of the ground.

The storage unit 43 of the diagnostic apparatus body 3 stores an operation program of the diagnostic apparatus body 3, and the like. As the storage unit 43, a recording medium, such as a flash memory, an HDD, an SSD, an FD, an MO disc, an MT, a RAM, a CD, a DVD, an SD card, or a USB memory, a server, or the like can be used.

The body controller 41 of the body processor 45 performs control of each unit of the diagnostic apparatus body 3 based on a program stored in advance in the storage unit 43 or the like, and an input operation of the user through the input device 42.

Although the body processor 45 having the transmission and reception unit 32, the transmission and reception controller 33, the ultrasound image generation unit 34, the communication controller 36, the navigation image generation unit 37, the measurement spot decision unit 38, the measurement procedure association unit 39, the ground derivation unit 40, and the body controller 41 is configured with a CPU and a control program causing the CPU to execute various kinds of processing, the body processor 45 may be configured using an FPGA, a DSP, an ASIC, a GPU, or other ICs or may be configured by combining the ICs.

The transmission and reception unit 32, the transmission and reception controller 33, the ultrasound image generation unit 34, the communication controller 36, the navigation image generation unit 37, the measurement spot decision unit 38, the measurement procedure association unit 39, the ground derivation unit 40, and the body controller 41 of the body processor 45 can also be configured to be partially or wholly integrated into one CPU or the like.

Next, an operation of the ultrasound diagnostic apparatus 1 according to Embodiment 1 of the invention to display a measurement spot of a subject S on the display unit 21 of the head-mounted display 2 will be described.

First, subject information including at least one of a symptom or a disease of the subject S is input by the user through the input device 42 of the diagnostic apparatus body 3. In this case, the subject information can be input as text data, voice data, or the like input by the user through the input device 42, for example. For example, the subject information can also be input by the user selecting a previous diagnostic result and the like of the subject S stored in the data memory 44 through the input device 42.

In a case where the subject information is input in this manner, the measurement spot decision unit 38 of the diagnostic apparatus body 3 estimates the part of the subject S and the status of the part related to any one of the symptom and the disease of the subject S from the input subject information and decides the measurement spot of the subject S based on the estimated part in the subject S and the estimated status of the part. Here, the measurement spot decision unit 38 can store the measurement spot correspondence table in which, for example, the symptom of the subject S, the part in the subject S related to the symptom, the status of the part in the subject S, and the measurement spot of the subject S correspond to one another, can estimate the part in the subject S and the status of the part from the subject information referring to the measurement spot correspondence table, and can decide the measurement spot of the subject S based on the estimated part in the subject S and the estimated status of the part.

In this way, the measurement spot of the subject S is automatically decided by the measurement spot decision unit 38 from the subject information input by the user through the input device 42, and thus, an appropriate measurement spot with respect to a symptom or a disease of the subject S is decided regardless of user's proficiency.

In a case where there is a given measurement procedure with respect to the part in the subject S and the status of the part estimated by the measurement spot decision unit 38 based on the input subject information, the measurement procedure association unit 39 of the diagnostic apparatus body 3 sends the measurement procedure to the navigation image generation unit 37 in association with the estimated part in the subject and the estimated status of the part. The measurement procedure association unit 39 can store a measurement procedure association table in which, for example, a given measurement procedure is associated with each of a plurality of parts in the subject and the statuses of a plurality of parts estimatable by the measurement spot decision unit 38 and can associate the measurement procedure with the part in the subject and the status of the part referring to the measurement procedure association table.

The ground derivation unit 40 of the diagnostic apparatus body 3 derives a description to be a ground for the decision of the measurement spot of the subject by the measurement spot decision unit 38 from the subject information received through the measurement spot decision unit 38 and sends the derived description to be the ground to the navigation image generation unit 37. The ground derivation unit 40 can derive the description to be the ground for the decision of the measurement spot by extracting a key word related to the measurement spot decided by the measurement spot decision unit 38, and the estimated part in the subject and the estimated status of the part from the subject information input by the user through the input device 42, for example. The ground derivation unit 40 can also derive the description to be the ground for the decision of the measurement spot by an inference based on the extracted keyword, for example.

Next, a camera image obtained by imaging the subject S positioned within a field of view in front of the user is captured by the camera unit 22 of the head-mounted display 2 mounted on the head of the user. The camera image acquired in this manner is transmitted to the diagnostic apparatus body 3 through the head-mounted display-side wireless communication unit 23 in a wireless manner. The camera image transmitted from the head-mounted display 2 in a wireless manner is sent to the navigation image generation unit 37 of the diagnostic apparatus body 3 through the body-side wireless communication unit 35.

The navigation image generation unit 37 recognizes the subject shown in the camera image received from the head-mounted display 2 through the body-side wireless communication unit 35 and generates a navigation image indicating a position of the measurement spot decided by the measurement spot decision unit 38 with respect to the recognized subject. In this case, the navigation image generation unit 37 can include information representing the measurement procedure associated with the part in the subject S and the status of the part by the measurement procedure association unit 39 and information representing the description of the ground derived by the ground derivation unit 40, in the navigation image as shown in FIG. 8. In the example shown in FIG. 8, the navigation image includes the measurement spot mark M positioned at the measurement spot of the subject S and the guide panel G1. In the guide panel G1, text data (not shown) representing the measurement procedure and text data (not shown) representing the description of the ground are included.

Here, in recognizing the subject from the camera image, the navigation image generation unit 37 can recognize the subject by storing typical pattern data of the subject as a template in advance, calculating a degree of similarity to pattern data while searching the inside of the camera image with the template, and considering that the subject is present at a place where the degree of similarity is equal to or greater than a threshold value and is the maximum. For the calculation of the degree of similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

The navigation image generated in this manner is transmitted to the head-mounted display 2 through the body-side wireless communication unit 35 in a wireless manner. The navigation image transmitted from the diagnostic apparatus body 3 in a wireless manner is sent to the display controller 25 through the head-mounted display-side wireless communication unit 23 and is displayed on the display unit 21 of the head-mounted display 2, for example, as shown in FIG. 8 under the control of the display controller 25. In the example shown in FIG. 8, the navigation image including the measurement spot mark M and the guide panel G1 is displayed on the display unit 21 to overlap the subject S viewed by the user through the transmissive display unit 21. The user brings the ultrasound probe 31 into contact with a body surface of the subject S such that the position and the direction of the ultrasound probe 31 match the measurement spot of the subject S shown in the navigation image displayed on the display unit 21, and performs ultrasonography of the subject S.

The measurement spot of the subject S where the transmission and reception of the ultrasonic wave by the ultrasound probe 31 is desired is displayed on the display unit 21 of the head-mounted display 2, and thus, the user can easily recognize the measurement spot of the subject S. The user can easily recognize the measurement procedure for measuring the part in the subject S and the status of the part related to the measurement spot and the description of the ground for the decision of the measurement spot, and thus, the user can easily perform ultrasonography of the subject S.

In this manner, the ultrasound diagnostic apparatus 1 ends the operation to display the measurement spot of the subject S on the display unit 21 of the head-mounted display 2.

From the above description, with the ultrasound diagnostic apparatus 1 according to Embodiment 1 of the invention, the measurement spot of the subject S is automatically decided based on the subject information input by the user through the input device 42 of the diagnostic apparatus body 3, and the decided measurement spot is displayed on the display unit 21 of the head-mounted display 2. Therefore, it is possible to allow the user to easily perform ultrasonography on the subject S regardless of user's proficiency.

Although the measurement spot decision unit 38 decides the measurement spot of the subject S based on the subject information, such as text data or voice data input from the user through the input device 42 or a previous diagnostic result of the subject S stored in the data memory 44, the measurement spot decision unit 38 can also extract a keyword related to at least one of the symptom or the disease of the subject from the subject information and decide a measurement spot of the subject S based on the extracted keyword. With this, even though information unrelated to the symptom or the disease of the subject S is included in the subject information, only information necessary for deciding the measurement spot of the subject S is extracted, and thus, the measurement spot decision unit 38 can decide a more appropriate measurement spot with respect to the symptom or the disease of the subject S.

The measurement spot decision unit 38 estimates the part in the subject S and the status of the part related to at least one of the symptom or the disease of the subject S from the subject information including at least one of the symptom or the disease of the subject S referring to the measurement spot correspondence table. For example, the part in the subject S and the status of the part can also be estimated using a method of so-called deep learning.

Although the measurement spot decision unit 38 decides the measurement spot of the subject S based on the subject information including at least one of the symptom or the disease of the subject S, the measurement spot decision unit 38 can also decide the measurement spot of the subject S, for example, based on at least one of a medical history, a status of treatment, a health status, or physical information of the subject S. With the use of the subject information including at least one of the symptom or the disease of the subject S, the measurement spot decision unit 38 can decide a more accurate measurement spot, for example, in a case where a symptom with high urgency, such as bleeding, appears in the subject S.

The measurement spot decision unit 38 can send, for example, text data representing the measurement spot, an image in which a mark representing the measurement spot, such as a body mark, is disposed on a general two-dimensional human model, or an image in which a mark representing the measurement spot is disposed on a general three-dimensional human model, as information representing the measurement spot of the subject S to the navigation image generation unit 37. Even though information representing the measurement spot is received in any format from the measurement spot decision unit 38, the navigation image generation unit 37 can generate a navigation image indicating the measurement spot.

The measurement spot decision unit 38 can store a given degree of urgency with respect to each of a plurality of estimatable parts in the subject S and the statuses of a plurality of parts, and can send the degree of urgency corresponding to the part in the subject S and the status of the part estimated from the subject information to the navigation image generation unit 37. Here, for example, as the urgency of the status of the part in the subject S is higher, such as a case where a part in the subject S is bleeding, the degree of urgency of the part is set to be higher. For example, a degree of urgency of a status in which the part in the subject S is calcified is set to be lower than a degree of urgency of a status in which the part in the subject S is bleeding.

In this manner, in a case where the degree of urgency of the part in the subject S and the status of the part is sent from the measurement spot decision unit 38 to the navigation image generation unit 37, the navigation image generation unit 37 can include information representing the degree of urgency of the part in the subject S and the status of the part related to the decided measurement spot, in the navigation image. In this case, for example, though not shown, the navigation image can include a mark, text data, or the like representing the degree of urgency. For example, in the navigation image, the measurement spot mark M indicating the measurement spot, or the like may have a given color representing the degree of urgency.

Figure 9:
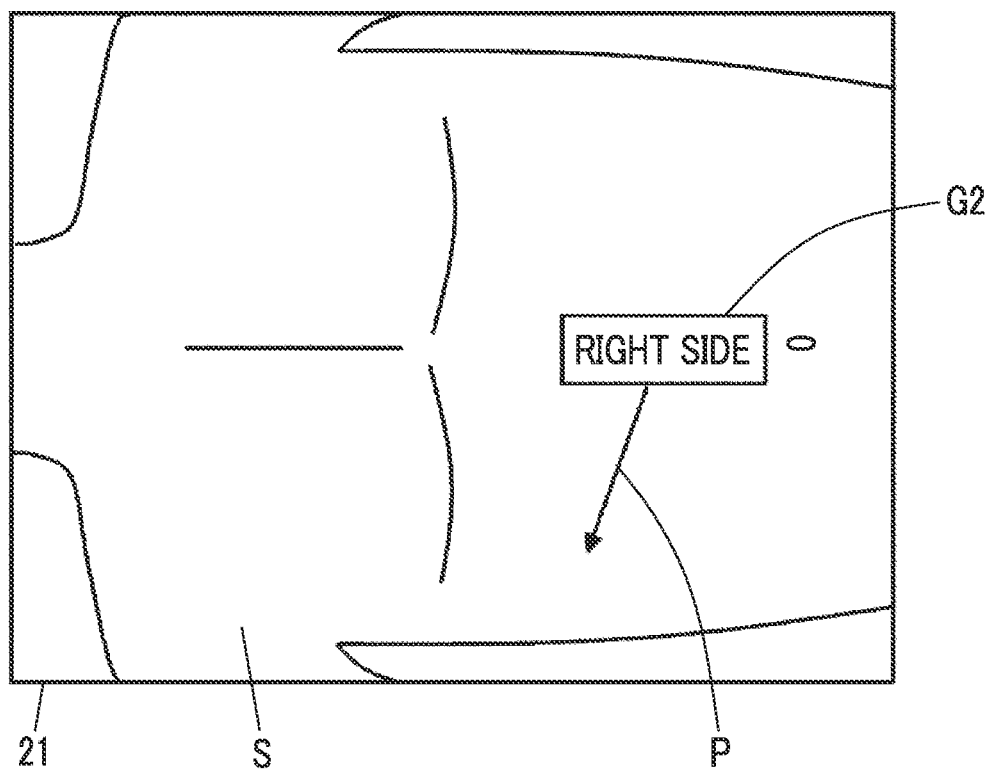
FIG. 9 is a diagram showing an example of a navigation image that includes an arrow indicating a measurement spot of the subject in Embodiment 1 of the invention.

As shown in FIGS. 7 and 8, although the navigation image includes the measurement spot mark M represented by the rectangularly closed broken line as indicating the measurement spot of the subject S, the shape and the size of the measurement spot mark M are not limited thereto. For example, the measurement spot mark M may have a circular shape or a polygonal shape or may be any closed curved shape. The measurement spot mark M is not limited as being formed with the broken line, and can also be formed with a solid line or can also be formed with a region colored with a given color. As indicating the measurement spot of the subject S, the navigation image can also include an arrow P shown in FIG. 9 instead of the measurement spot mark M. In the example shown in FIG. 9, a navigation image includes a guide panel G2 that is connected to a based end of the arrow P and indicates "right side" as the name of the measurement spot.

Although the measurement spot decision unit 38 estimates the part in the subject S and the status of the part from the input subject information, and decides the measurement spot of the subject S based on the estimated part in the subject S and the estimated status of the part, the same measurement spot may be decided from a plurality of combinations of the part in the subject S and the status of the part. For example, the measurement spot decision unit 38 may decide "below solar plexus" as the same measurement spot based on the combination of "gallbladder" and "gallbladder inflammation" and the combination of "pancreas" and "pancreatitis" as the combination of the part in the subject S and the status of the part. In such a case, for example, with respect to different combinations of the part in the subject S and the status of the part, such as the combination of "gallbladder" and "gallbladder inflammation" and the combination of "pancreas" and "pancreatitis", measurement procedures associated by the measurement procedure association unit 39 and descriptions to be grounds derived by the ground derivation unit 40 may be different.

Figure 10:
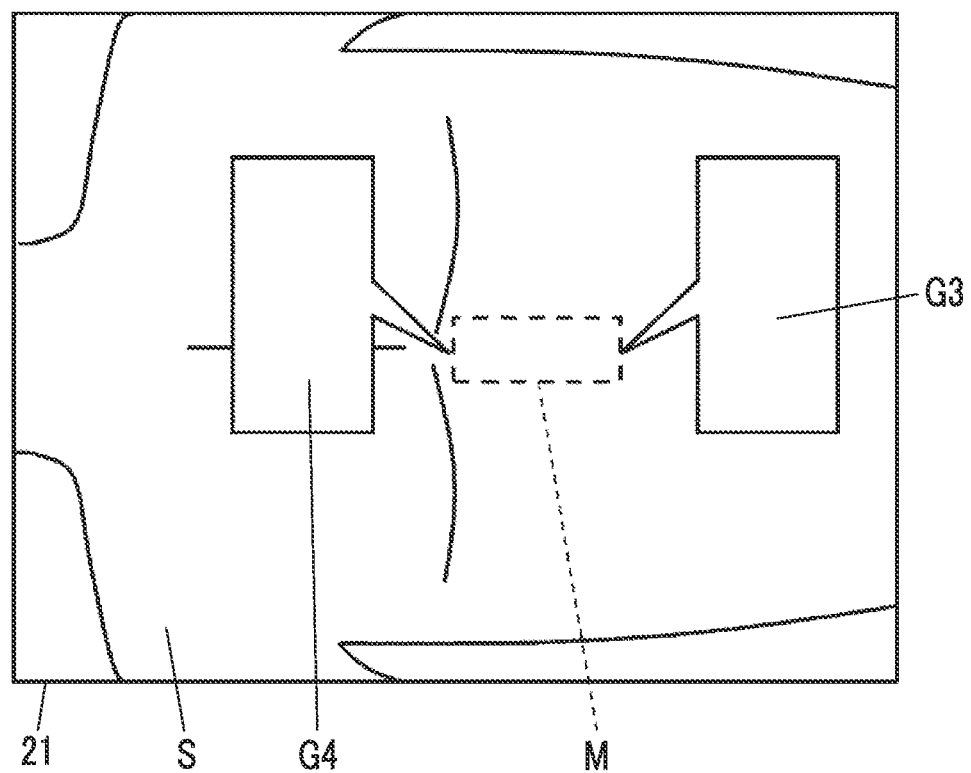
FIG. 10 is a diagram showing an example of a navigation image that includes a plurality of guide panels in Embodiment 1 of the invention.

For this reason, for example, as shown in FIG. 10, the navigation image generation unit 37 can include a plurality of guide panels G3 and G4 in the subject S with respect to one measurement spot in a navigation image. In the example shown in FIG. 10, the navigation image includes two guide panels G3 and G4 extending from a measurement spot mark M positioned below the solar plexus of the subject S. Though not shown, the guide panel G3 includes, for example, text data representing "gallbladder" as a name of a part in the subject S, text data representing "gallbladder inflammation" as a status of "gallbladder", text data representing a measurement procedure for measuring "gallbladder inflammation", and text data representing a description to be a ground for the decision of "below solar plexus" as a measurement spot from "gallbladder" and "gallbladder inflammation". Though not shown, the guide panel G4 includes, for example, text data representing "pancreas" as a name of the part in the subject S, text data representing "pancreatitis" as a status of "pancreas", text data representing a measurement procedure for measuring "pancreatitis", and text data representing a description to be a ground for the decision of "below solar plexus" as a measurement spot from "pancreas" and "pancreatitis".

In this way, the navigation image includes information related to a plurality of parts in the subject S and the statuses of a plurality of parts with respect to one measurement spot, whereby the user can easily recognize a plurality of parts in the subject S and the statuses of a plurality of parts related to the symptom or the disease of the subject S with respect to the one measurement spot and can perform appropriate measurement.

Figure 11:
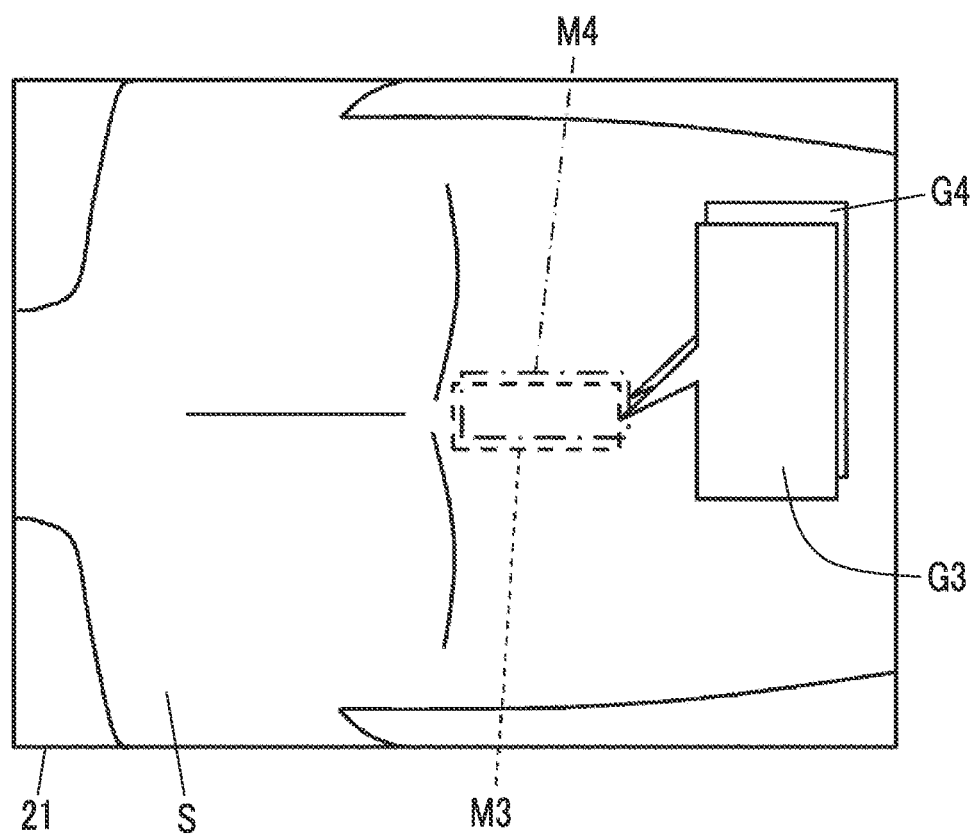
FIG. 11 is a diagram showing an example of a navigation image that includes a plurality of measurement spot marks and a plurality of guide panels in Embodiment 1 of the invention.

As in a case where two parts "gallbladder" and "pancreas" are related to "below solar plexus", a plurality of parts in the subject S and the statuses of a plurality of parts may be related to one measurement spot. In such a case, the navigation image generation unit 37 can consider one measurement spot as a plurality of independent measurement spots related to a plurality of parts in the subject S and the statuses of a plurality of parts, such as "below solar plexus" related to "gallbladder" and "below solar plexus" related to "pancreas", for example, and can include the measurement spot marks M or the like indicating the measurement spots in the navigation image. For example, as shown in FIG. 11, the navigation image generation unit 37 can include a measurement spot mark M3 indicating "below solar plexus" regarding "gallbladder" and a measurement spot mark M4 indicating "below solar plexus" regarding "pancreas" in the navigation image. The measurement spot mark M3 and the measurement spot mark M4 are disposed to partially overlap each other.

In the example shown in FIG. 11, the navigation image includes a guide panel G3 that is connected to the measurement spot mark M3 and includes text data representing "gallbladder", and a guide panel G4 that is connected to the measurement spot mark M4 and includes text data representing "pancreas". Although the guide panel G3 is disposed to partially overlap the guide panel G4, for example, the navigation image generation unit 37 can replace a vertical relationship between the guide panel G3 and the guide panel G4 based on an input operation of the user through the input device 42.

As shown in FIGS. 8, 10, and 11, although the navigation image includes information representing the measurement procedures associated by the measurement procedure association unit 39 and information representing the descriptions to be the grounds for the decision of the measurement spots derived by the ground derivation unit 40 in the guide panels G1, G3, and G4, information representing the measurement procedures and information representing the descriptions to be the grounds for the decision of the measurement spots are not limited as being included in the guide panels G1, G3, and G4. For example, though not shown, the navigation image can position a list of information representing the measurement procedures and the descriptions to be the grounds for the decision of the measurement spots near the measurement spots instead of the guide panels G1, G3, and G4.

Although the diagnostic apparatus body 3 has the data memory 44 that is connected to the body controller 41 and stores the subject information, for example, an external server that is connected to an external network, such as a network in a hospital, and stores an electronic medical chart and the like of a subject can also be connected to the body controller 41. In this case, the user can input the electronic medical chart and the like of the subject stored in the external server as subject information to the body controller 41 by an input operation through the input device 42.

Although a case where the display unit 21 of the head-mounted display 2 has transmittance has been exemplified, the display unit 21 may not have transmittance. In this case, for example, though not shown, the camera unit 22 and the display controller 25 are connected, and the camera image acquired by the camera unit 22 is displayed on the display unit 21 of the head-mounted display 2, whereby the user can view the field of view in front of the user displayed on the display unit 21. In this case, the navigation image generation unit 37 can include the camera image in the navigation image, for example, by generating an image in which the measurement spot mark M shown in FIG. 7 is superimposed on the camera image, as a navigation image. With this, even though the display unit 21 of the head-mounted display 2 does not have transmittance, similarly to a case where the display unit 21 has transmittance, the user can easily recognize the measurement spot of the subject S. Therefore, it is possible to allow the user to easily perform ultrasonography on the subject S regardless of proficiency.

As shown in FIG. 6, although the ultrasound image generation unit 34 has the B mode image generation unit 56 and the Doppler image generation unit 57, the ultrasound image generation unit 34 can further have an M mode image generation unit that generates a so-called M mode image, an elastic map image generation unit that generates a so-called elastic map image, a sound speed map image generation unit that generates a so-called sound speed map image, and the like. In this case, the ultrasound diagnostic apparatus 1 can have a mode where the M mode image is generated, a mode where the elastic map image is generated, a mode where the sound speed map image is generated, and the like, in addition to a mode where the B mode image is generated and a mode where the Doppler image is generated. In this way, even though the ultrasound diagnostic apparatus 1 has a plurality of observation modes, with the ultrasound diagnostic apparatus 1 of Embodiment 1 of the invention, an appropriate measurement spot is decided based on the subject information. Therefore, it is possible to allow the user to easily perform ultrasonography of the subject S regardless of user's proficiency.

The diagnostic apparatus body 3 can be configured as a stationary apparatus, such as a so-called tower type, or can also be configured as a portable apparatus, such as a so-called tablet type or a laptop type. In this way, the form of the diagnostic apparatus body 3 is not particularly limited.

Although the head-mounted display 2 and the diagnostic apparatus body 3 are connected in a wireless state, so-called wired connection may be made. In the diagnostic apparatus body 3, the ultrasound probe 31 and the body processor 45 can also be connected in a wireless state.

In this way, with the ultrasound diagnostic apparatus 1 of Embodiment 1 of the invention, no matter which form the diagnostic apparatus body 3 has and no matter which connection aspect each unit of the ultrasound diagnostic apparatus 1 has, the user can perform ultrasonography on the subject S regardless of user's proficiency.

Although the body processor 45 of the diagnostic apparatus body 3 includes the transmission and reception unit 32, the transmission and reception controller 33, and the ultrasound image generation unit 34, the transmission and reception unit 32, the transmission and reception controller 33, and the ultrasound image generation unit 34 can be included in the ultrasound probe 31, instead of being included in the body processor 45. In this case, for example, the transmission and reception unit 32, the transmission and reception controller 33, and the ultrasound image generation unit 34 included in the ultrasound probe 31 configure a probe processor (not shown). The ultrasound image generated by the ultrasound image generation unit 34 of the ultrasound probe 31 is transmitted to the head-mounted display 2, for example, through the body-side wireless communication unit 35 in a wireless manner.

Although the body processor 45 of the diagnostic apparatus body 3 includes the navigation image generation unit 37, the measurement spot decision unit 38, the measurement procedure association unit 39, and the ground derivation unit 40, the navigation image generation unit 37, the measurement spot decision unit 38, the measurement procedure association unit 39, and the ground derivation unit 40 can be included in the head-mounted display processor 27 of the head-mounted display 2, instead of being included in the body processor 45.

In this case, the subject information input by the user through the input device 42 is transmitted to the head-mounted display 2 through the body-side wireless communication unit 35 in a wireless manner, and the subject information transmitted in a wireless manner is received by the measurement spot decision unit 38 of the head-mounted display processor 27 through the head-mounted display-side wireless communication unit 23. The measurement spot decision unit 38 decides a measurement spot of the subject S based on the received subject information, and information representing the decided measurement spot is sent to the navigation image generation unit 37. The navigation image generation unit 37 generates a navigation image indicating the measurement spot of the subject S based on information representing the measurement spot of the subject S received from the measurement spot decision unit 38 and the camera image acquired by the camera unit 22. The navigation image generated in this manner is displayed on the display unit 21 of the head-mounted display 2 through the display controller 25.

In this way, even though the head-mounted display processor 27 of the head-mounted display 2 includes the navigation image generation unit 37, the measurement spot decision unit 38, the measurement procedure association unit 39, and the ground derivation unit 40, similarly to a case where the body processor 45 of the diagnostic apparatus body 3 includes the navigation image generation unit 37, the measurement spot decision unit 38, the measurement procedure association unit 39, and the ground derivation unit 40, the navigation image indicating the measurement spot of the subject S is generated, and the generated navigation image is displayed on the display unit 21 of the head-mounted display 2. Therefore, it is possible to allow the user to easily perform ultrasonography on the subject S regardless of user's proficiency.

For example, the transmission and reception unit 32, the transmission and reception controller 33, the ultrasound image generation unit 34, the navigation image generation unit 37, the measurement spot decision unit 38, the measurement procedure association unit 39, the ground derivation unit 40, the input device 42, the storage unit 43, and the data memory 44 provided in the diagnostic apparatus body 3 can be provided in the head-mounted display 2, and the diagnostic apparatus body 3 can be omitted. In this case, though not shown, the head-mounted display processor is configured with the communication controller 24, the display controller 25, the head-mounted display controller 26, the transmission and reception unit 32, the transmission and reception controller 33, the ultrasound image generation unit 34, the navigation image generation unit 37, the measurement spot decision unit 38, the measurement procedure association unit 39, and the ground derivation unit 40. The input device 42, the storage unit 43, and the data memory 44 are connected to the head-mounted display controller 26. As the input device 42, for example, a microphone is used.

In this case, for example, the head-mounted display 2 and the ultrasound probe 31 are connected by wireless communication.

In a case where the transmission and reception unit 32, the transmission and reception controller 33, the ultrasound image generation unit 34, the navigation image generation unit 37, the measurement spot decision unit 38, the measurement procedure association unit 39, the ground derivation unit 40, the input device 42, the storage unit 43, and the data memory 44 are provided in the head-mounted display 2, a measurement spot of the subject S is decided by the measurement spot decision unit 38 based on the subject information input by the user through the input device 42 of the head-mounted display 2, and information representing the decided measurement spot of the subject S is sent to the navigation image generation unit 37. The navigation image generation unit 37 generates a navigation image based on information representing the measurement spot of the subject S and the camera image acquired by the camera unit 22. The generated navigation image is displayed on the display unit 21 of the head-mounted display 2 through the display controller 25.

The transmission and reception unit 32 of the head-mounted display 2 transmits a drive signal for driving the transducer array 31A of the ultrasound probe 31 to the ultrasound probe 31 through the head-mounted display-side wireless communication unit 23, and receives a reception signal acquired by the transmission and reception of the ultrasonic wave to and from the subject by the ultrasound probe, through the head-mounted display-side wireless communication unit 23. The transmission and reception unit 32 executes various kinds of processing on the received reception signal to generate digital data. The ultrasound image generation unit 34 generates an ultrasound image based on the digital data generated by the transmission and reception unit 32, and the generated ultrasound image is displayed on the display unit 21 of the head-mounted display 2 through the display controller 25.

In this way, even though the head-mounted display 2 comprises the transmission and reception unit 32, the transmission and reception controller 33, the ultrasound image generation unit 34, the navigation image generation unit 37, the measurement spot decision unit 38, the measurement procedure association unit 39, the ground derivation unit 40, the input device 42, the storage unit 43, and the data memory 44, and the diagnostic apparatus body 3 is omitted, similarly to a case where the diagnostic apparatus body 3 comprises the transmission and reception unit 32, the transmission and reception controller 33, the ultrasound image generation unit 34, the navigation image generation unit 37, the measurement spot decision unit 38, the measurement procedure association unit 39, the ground derivation unit 40, the input device 42, the storage unit 43, and the data memory 44, the navigation image indicating the measurement spot of the subject S is generated, and the generated navigation image is displayed on the display unit 21 of the head-mounted display 2. Therefore, it is possible to allow the user to easily perform ultrasonography on the subject S regardless of user's proficiency.

For example, while the ultrasound probe 31 can comprise the transmission and reception unit 32, the transmission and reception controller 33, and the ultrasound image generation unit 34, and the head-mounted display 2 can comprise the navigation image generation unit 37, the measurement spot decision unit 38, the measurement procedure association unit 39, and the ground derivation unit 40, the diagnostic apparatus body 3 can be omitted. Even in this case, similarly to a case where the diagnostic apparatus body 3 comprises the transmission and reception unit 32, the transmission and reception controller 33, the ultrasound image generation unit 34, the navigation image generation unit 37, the measurement spot decision unit 38, the measurement procedure association unit 39, and the ground derivation unit 40, the navigation image indicating the measurement spot of the subject S is generated, and the generated navigation image is displayed on the display unit 21 of the head-mounted display 2. Therefore, it is possible to allow the user to easily perform ultrasonography on the subject S regardless of user's proficiency.

Embodiment 2

In Embodiment 1, although the measurement spot decision unit 38 decides one measurement spot based on the input subject information, the measurement spot decision unit 38 can also decide a plurality of measurement spots. In this case, for example, the measurement spot decision unit 38 stores a measurement spot correspondence table in which candidates of a plurality of parts in the subject S and candidates of the statuses of a plurality of parts relatable correspond to one symptom, and decides a plurality of measurement spots from the subject information referring to the stored measurement spot correspondence table.

For example, in a case where symptoms "abdominal pain" and "back pain" are included in the input subject information, "gallbladder", "pancreas", and "abdominal aorta" correspond as the candidates of the parts in the subject S related to "abdominal pain" and "back pain" in the measurement spot correspondence table. Then, "gallbladder inflammation" and "gallstone" can correspond as the candidates of the status of "gallbladder", "pancreatitis" and "pancreatic cancer" can correspond as the candidates of the status of "pancreas", and "abdominal aortic aneurysm" can correspond as the candidate of the status of "abdominal aorta" in the measurement spot correspondence table. As candidates of the measurement spot of the subject S, for example, "right subcostal" can correspond to a combination of "gallbladder" and "gallbladder inflammation" and a combination of "gallbladder" and "gallstone", "below solar plexus" can correspond to a combination of "pancreas" and "pancreatitis" and a combination of "pancreas" and "pancreatic cancer", and "below solar plexus to navel" can correspond to a combination of "abdominal aorta" and "abdominal aortic aneurysm" in the measurement spot correspondence table.

In a case where such correspondence is made in the measurement spot correspondence table, the measurement spot decision unit 38 can decide each of three candidates of the measurement spot of "right subcostal", "below solar plexus", and "below solar plexus to navel" estimated from a plurality of parts in the subject S and the statues of the parts with respect to, for example, the symptoms "abdominal pain" and "back pain", as the measurement spot of the subject S.

In a case where a plurality of measurement spots are decided by the measurement spot decision unit 38 in this manner, the navigation image generation unit 37 generates a navigation image indicating a plurality of measurement spots.

Figure 12:
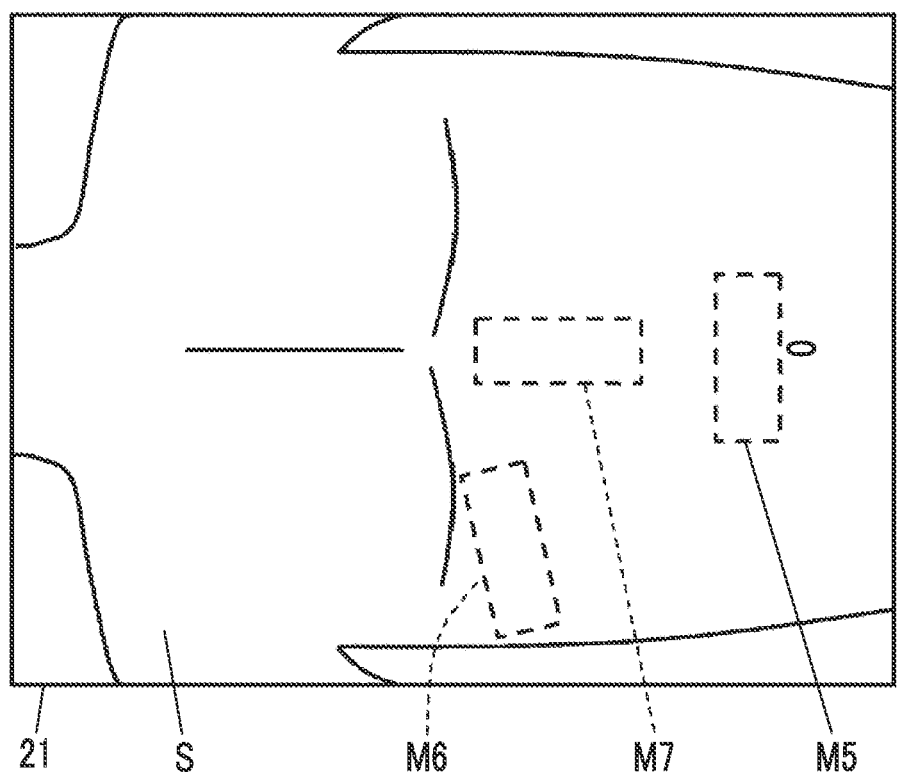
FIG. 12 is a diagram showing an example of a navigation image that includes a plurality of measurement spot marks of the subject in Embodiment 2 of the invention.

For example, as shown in FIG. 12, the navigation image generation unit 37 can include a measurement spot mark M5 indicating "below solar plexus to navel", measurement spot mark M6 indicating "right subcostal", and a measurement spot mark M7 indicating "below solar plexus", in the navigation image. Though not shown, the navigation image generation unit 37 can position a guide panel that includes information representing the part in the subject S and the status of the part estimated by the measurement spot decision unit 38, information representing the measurement procedure associated by the measurement procedure association unit 39, and information representing the description to be the ground for the decision of the measurement spot derived by the ground derivation unit 40, near each of a plurality of measurement spot marks.

As described above, even though a plurality of measurement spots are decided by the measurement spot decision unit 38, similarly to a case where only one measurement spot is decided by the measurement spot decision unit 38, the user can easily recognize the measurement spot of the subject S to easily perform ultrasonography of the subject S.

In a case where a plurality of candidates of the measurement spot are derived from the input subject information, the measurement spot decision unit 38 can decide the measurement spot of the subject S by narrowing down a plurality of derived candidates of the measurement spot to leave candidates of the measurement spot having high relevance with the symptom or the disease of the subject S. For example, in a case where a plurality of symptoms of the subject S are input as subject information, the measurement spot decision unit 38 can give a higher evaluation value to a plurality of candidates of the measurement spot as the number of related symptoms is greater, and can narrow down a plurality of candidates of the measurement spot to leave candidates of the measurement spot where the evaluation value is equal to or greater than a given threshold value.

For example, in a case where three symptoms "abdominal pain", "back pain", and "fever" are input as subject information, the measurement spot decision unit 38 can give, as the evaluation value, three points to the candidates of the measurement spot related to the three symptoms of "abdominal pain", "back pain", and "fever", two points to the candidates of the measurement spot related to two symptoms of "abdominal pain", "back pain", and "fever", and one point to the candidates of the measurement spot related to any one of "abdominal pain", "back pain", and "fever". For example, in a case where the given threshold value of the evaluation value is two points, the measurement spot decision unit 38 can narrow down a plurality of candidates of the measurement spot to leave the candidates of the measurement spot related to two or more symptoms of "abdominal pain", "back pain", and "fever".

In this manner, the measurement spot decision unit 38 narrows down a plurality of candidates of the measurement spot, whereby the user can easily recognize the measurement spot having higher relevance with the symptom or the disease of the subject.

The measurement spot decision unit 38 can store a degree of urgency to each of a plurality of estimatable parts in the subject S and the estimatable statuses of a plurality of parts, and can give priority to a plurality of measurement spots of the subject S related to the part in the subject S and the status of the part based on the degree of urgency corresponding to the part in the subject S and the status of the part estimated from the subject information. For example, priority of a measurement spot related to a part being bleeding is set to be higher than priority of a measurement spot related to a part being calcified.

Figure 13:
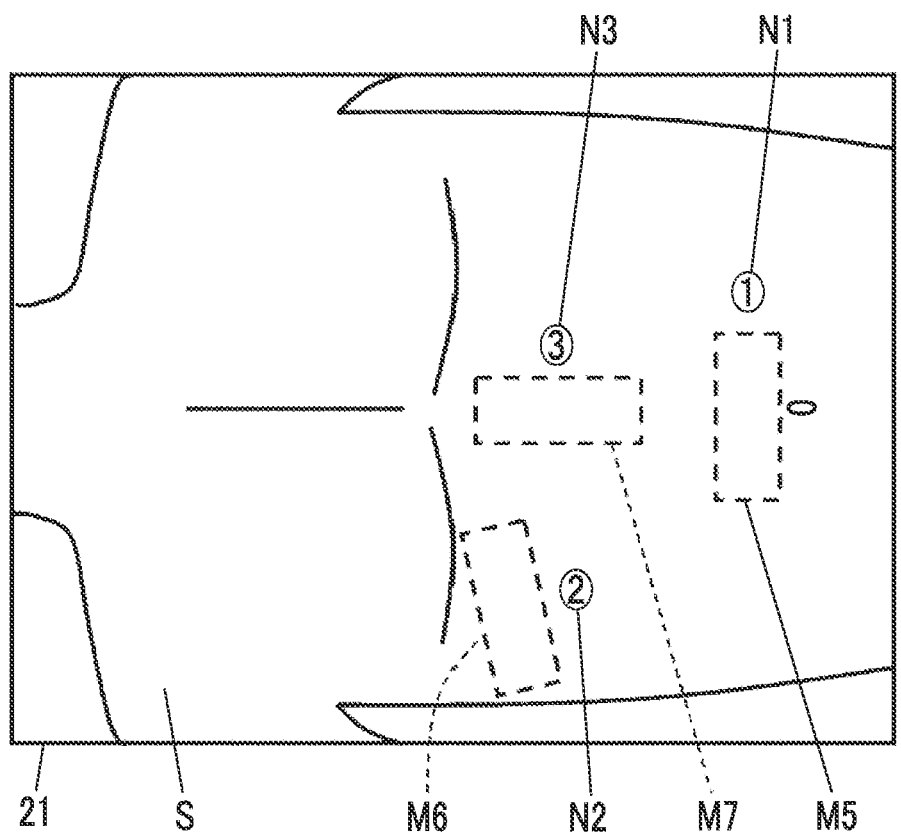
FIG. 13 is a diagram showing an example of a navigation image in which a plurality of measurement spots of the subject are given priority in Embodiment 2 of the invention.

In a case where the measurement spot decision unit 38 gives the priority to a plurality of measurement spots of the subject S, the navigation image generation unit 37 generates a navigation image with a plurality of measurement spots given priority. For example, as shown in FIG. 13, the navigation image generation unit 37 can dispose numbers N1, N2, and N3 representing priority near respective measurement spots in the navigation image.

In the example shown in FIG. 13, the number N1 representing the first priority is disposed near the measurement spot mark M5 indicating "below solar plexus to navel", the number N2 representing the second priority is disposed near the measurement spot mark M6 indicating "right subcostal", and the number N3 representing the third priority is disposed near the measurement spot mark M7 indicating "below solar plexus". Though not shown, for example, a plurality of measurement spot marks M5 to M7 can also be colored with given colors depending on the priority.

In this manner, the navigation image generation unit 37 generates the navigation image with a plurality of measurement spots given priority, whereby the user can easily recognize the priority of a plurality of measurement spots.

Embodiment 3

In Embodiment 1, although the subject S is recognized from the camera image, and the navigation image indicating the measurement spot with respect to the recognized subject S is generated, the ultrasound probe 31 can be further detected from the camera image, and guidance about ultrasonography can be performed for the user corresponding to the position of the detected ultrasound probe 31.

Figure 14:
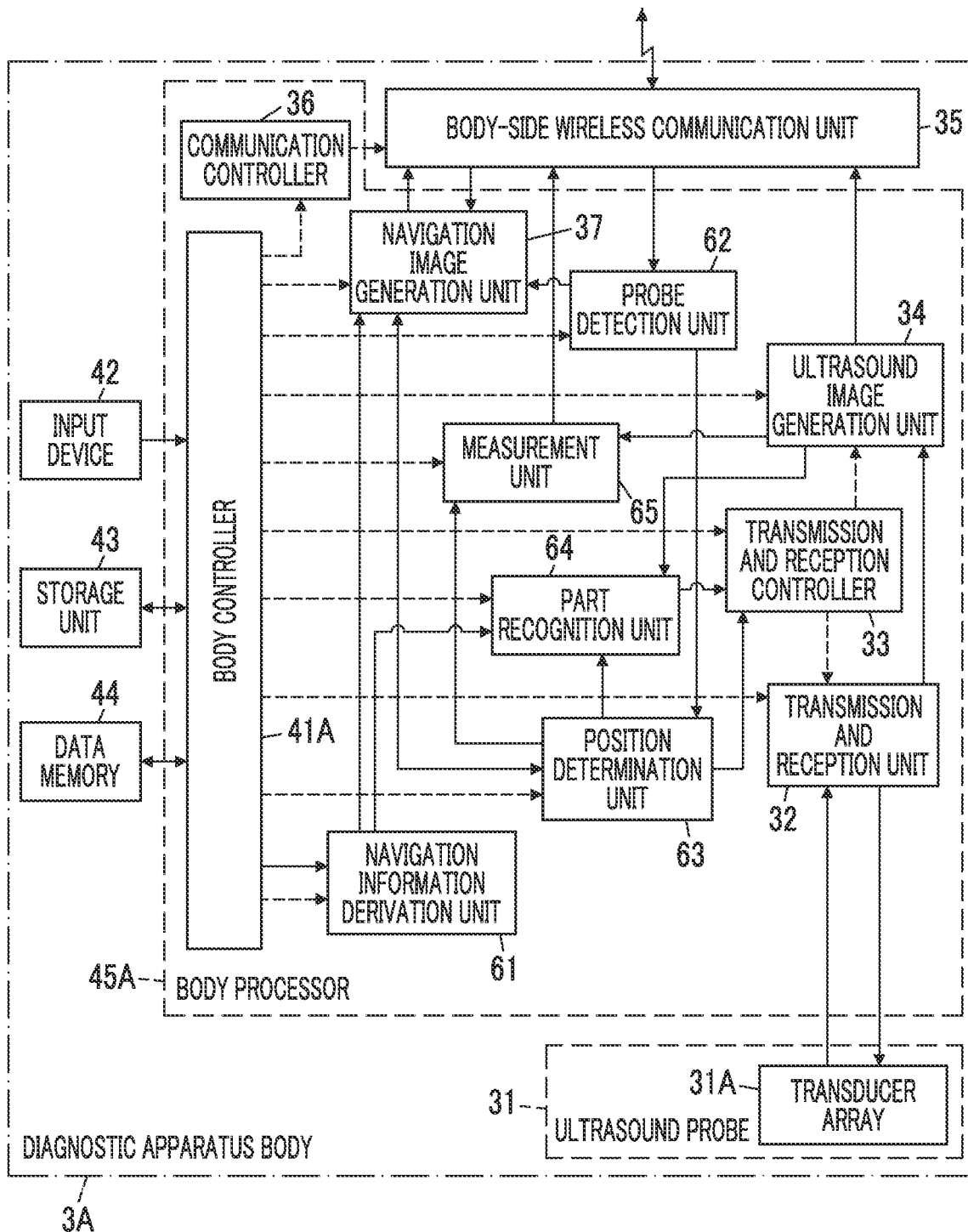
FIG. 14 is a block diagram showing the configuration of a diagnostic apparatus body in Embodiment 3 of the invention.
Figure 15:
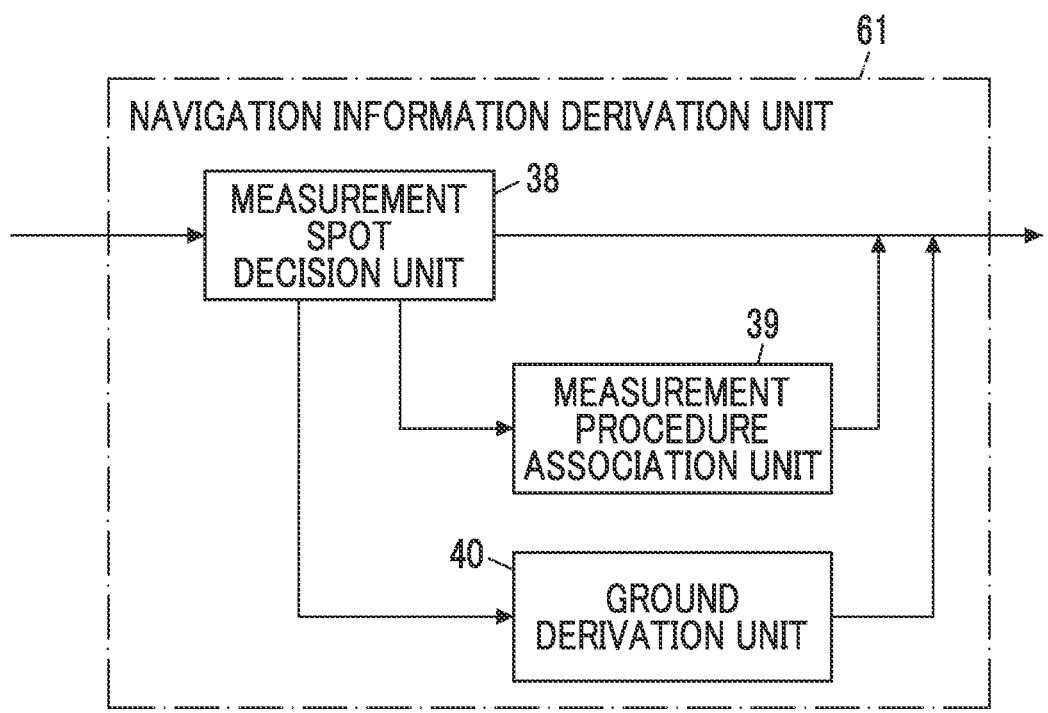
FIG. 15 is a block diagram showing the configuration of a navigation information derivation unit in Embodiment 3 of the invention.

As shown in FIG. 14, a diagnostic apparatus body 3A in Embodiment 3 comprises a navigation information derivation unit 61, a probe detection unit 62, a position determination unit 63, a part recognition unit 64, and a measurement unit 65, and comprises a body controller 41A instead of the body controller 41, compared to the diagnostic apparatus body 3 in Embodiment 1 shown in FIG. 4. Here, as shown in FIG. 15, the navigation information derivation unit 61 is configured with the measurement spot decision unit 38, the measurement procedure association unit 39, and the ground derivation unit 40, and for description, the measurement spot decision unit 38, the measurement procedure association unit 39, and the ground derivation unit 40 are put together into one unit.

As shown in FIG. 14, in the diagnostic apparatus body 3A, the navigation information derivation unit 61 is connected to the navigation image generation unit 37. The probe detection unit 62 is connected to the body-side wireless communication unit 35, and the navigation image generation unit 37 and the position determination unit 63 are connected to the probe detection unit 62. The transmission and reception controller 33, the navigation image generation unit 37, the part recognition unit 64, and the measurement unit 65 are connected to the position determination unit 63. The ultrasound image generation unit 34, the transmission and reception controller 33, and the navigation information derivation unit 61 are connected to the part recognition unit 64. The ultrasound image generation unit 34 is connected to the measurement unit 65.

The body controller 41A is connected to the transmission and reception controller 33, the ultrasound image generation unit 34, the communication controller 36, the navigation image generation unit 37, the navigation information derivation unit 61, the probe detection unit 62, the position determination unit 63, the part recognition unit 64, and the measurement unit 65. The transmission and reception unit 32, the transmission and reception controller 33, the ultrasound image generation unit 34, the communication controller 36, the navigation image generation unit 37, the body controller 41A, the navigation information derivation unit 61, the probe detection unit 62, the position determination unit 63, the part recognition unit 64, and the measurement unit 65 configure a body processor 45A.

The navigation information derivation unit 61 of the body processor 45A sends navigation information for guiding the user about ultrasonography of the subject S, such as the measurement spot of the subject S, the part in the subject S and the status of the part related to the measurement spot of the subject S, the measurement procedure related to the measurement spot, and the description to be the ground for the decision of the measurement spot, to the navigation image generation unit 37. As shown in FIG. 15, the navigation information derivation unit 61 includes the measurement spot decision unit 38, the measurement procedure association unit 39, and the ground derivation unit 40. The measurement spot decision unit 38 is connected to the measurement procedure association unit 39 and the ground derivation unit 40.

The probe detection unit 62 of the body processor 45A detects the ultrasound probe 31 from the camera image acquired by the camera unit 22 of the head-mounted display 2. The probe detection unit 62 can detect the ultrasound probe 31 from the camera image, for example, by performing so-called template matching or the like.

The position determination unit 63 of the body processor 45A determines whether or not the position of the measurement spot of the subject S indicated by the navigation image generated by the navigation image generation unit 37 overlaps the position of the ultrasound probe 31 detected by the probe detection unit 62. For example, the position determination unit 63 determines that the position of the measurement spot of the subject S overlaps the position of the ultrasound probe 31 in a case where the measurement spot mark M shown in FIG. 7 overlaps the position of the ultrasound probe 31 detected by the probe detection unit 62 by a given area or more, and determines that the position of the measurement spot of the subject S does not overlap the position of the ultrasound probe 31 in a case where the measurement spot mark M overlaps the position of the ultrasound probe 31 only by less than the given area and in a case where the measurement spot mark M does not completely overlap the position of the ultrasound probe 31.

The part recognition unit 64 of the body processor 45A recognizes a part in the subject S from the ultrasound image generated by the ultrasound image generation unit 34. The part recognition unit 64 can recognize the part in the subject S from the ultrasound image, for example, by performing so-called template matching or the like. In a case where the position determination unit 63 determines that the position of the measurement spot of the subject S overlaps the position of the ultrasound probe 31, the part recognition unit 64 can automatically recognize a part in the subject S related to the measurement spot where the ultrasound probe 31 is positioned, from the ultrasound image generated by the ultrasound image generation unit 34 at that time.

The measurement unit 65 of the body processor 45A performs measurement regarding the part in the subject S, for example, the length, the area, and the like of the part in the subject S in the B mode image based on the ultrasound image generated by the ultrasound image generation unit 34. The measurement unit 65 can perform measurement regarding the part in the subject S based on an input operation of the user through the input device 42.

In a case where the part in the subject S is recognized by the part recognition unit 64, the measurement unit 65 can also automatically perform measurement of the part in the subject S recognized by the part recognition unit 64 under a measurement condition corresponding to the part in the subject S recognized by the part recognition unit 64. For example, in a case where the measurement spot decided by the measurement spot decision unit 38 is "below solar plexus to navel", and a part in the subject S related to "below solar plexus to navel" is "inferior vena cava", the measurement unit 65 can automatically measure the diameter of the inferior vena cava from the B mode image generated by the ultrasound image generation unit 34.

In this way, in a case where the part in the subject S is recognized by the part recognition unit 64, the measurement unit 65 automatically performs measurement of the part in the subject S under the measurement condition corresponding to the part in the subject S recognized by the part recognition unit 64, whereby it is possible to reduce user's labor in ultrasonography.

For example, in a case where the position determination unit 63 determines that the position of the measurement spot of the subject S overlaps the position of the ultrasound probe 31, the transmission and reception controller 33 can control the transmission and reception of the ultrasonic wave by the transducer array 31A of the ultrasound probe 31 in compliance with the transmission and reception condition and the observation mode corresponding to the measurement spot where the ultrasound probe 31 is positioned. Here, the transmission and reception controller 33 can control the transmission and reception of the ultrasonic wave in compliance with the transmission and reception condition and the observation mode corresponding to the measurement spot where the ultrasound probe 31 is positioned, for example, by storing the transmission and reception conditions and the observation modes corresponding to a plurality of measurement spots in advance.

For example, in a case where the part in the subject S is recognized by the part recognition unit 64, the transmission and reception controller 33 can also control the transmission and reception of the ultrasonic wave by the transducer array 31A of the ultrasound probe 31 in compliance with the transmission and reception condition and the observation mode corresponding to the part in the subject S recognized by the part recognition unit 64. Here, the transmission and reception controller 33 can control the transmission and reception of the ultrasonic wave in compliance with the transmission and reception condition and the observation mode corresponding to the part in the subject S recognized by the part recognition unit 64, for example, by storing the transmission and reception conditions and the observation modes corresponding to a plurality of parts in the subject S estimatable by the measurement spot decision unit 38 in advance.

In a case where the position determination unit 63 determines that the position of the measurement spot of the subject S overlaps the position of the ultrasound probe 31, the body controller 41A controls each unit of the diagnostic apparatus body 3A to perform the measurement of the subject S in compliance with the measurement procedure related to the measurement spot where the ultrasound probe 31 is positioned and associated with the measurement procedure association unit 39.

For example, in a case where the position determination unit 63 determines that a position of "apex" of the subject S in the navigation image overlaps the position of the ultrasound probe 31, a part in the subject S related to "apex" is "heart", a status of "heart" is "mitral regurgitation", and an associated measurement procedure is "a B mode image is acquired, a color Doppler image is acquired, pulmonary regurgitation area measurement by proximal isovelocity surface area (PISA) method is performed, a Doppler image is acquired by a pulse Doppler method, and a regurgitant flow rate is measured", first, to obtain the B mode image, the body controller 41A makes the transmission and reception controller 33 control the transmission and reception of the ultrasonic wave by the transducer array 31A in compliance with the observation mode for acquiring the B mode image.

In this state, the B mode image displayed on the display unit 21 of the head-mounted display 2 is so-called freeze-displayed, for example, by the user through the input device 42, and in a case where the freeze-displayed B mode image is saved in the data memory 44 of the diagnostic apparatus body 3A, or the like, the body controller 41A makes the transmission and reception controller 33 control the transmission and reception of the ultrasonic wave by the transducer array 31A to execute the next procedure, that is, in compliance with the observation mode for acquiring the color Doppler image.

Next, in a case where the user freeze-displays the color Doppler image through the input device 42, the body controller 41A makes the measurement unit 65 perform measurement of the pulmonary regurgitation area by the so-called PISA method. In a case where the freeze-display of the color Doppler image is released by an input operation of the user through the input device 42, the body controller 41A makes the transmission and reception controller 33 control the transmission and reception of the ultrasonic wave by the transducer array 31A in compliance with the observation mode for acquiring the Doppler image by the so-called pulse Doppler method. Next, in a case where the acquired Doppler image is freeze-displayed by the user, the body controller 41A makes the measurement unit 65 perform measurement of the regurgitant flow rate based on the freeze-displayed Doppler image.

In this way, the body controller 41A controls each unit of the diagnostic apparatus body 3A to perform measurement of the subject S in compliance with the measurement procedure related to the measurement spot where the ultrasound probe 31 is positioned, whereby it is possible to allow the user to easily perform ultrasonography of the subject S regardless of user's proficiency.

In a case where the position determination unit 63 determines that the position of the measurement spot of the subject S overlaps the position of the ultrasound probe 31, the navigation image generation unit 37 can generate a navigation image in which a state in which the ultrasound probe 31 is positioned at the measurement spot is highlighted. For example, though not shown, the navigation image generation unit 37 can highlight a state in which the ultrasound probe 31 is positioned at the measurement spot, by coloring the measurement spot mark indicating the measurement spot where the ultrasound probe 31 is positioned, with a given color, in a case where the measurement spot mark is formed with a broken line, changing the broken line to a solid line or the like, or disposing text data representing that the ultrasound probe 31 is positioned, near the measurement spot. With this, the user can more clearly recognize that the ultrasound probe 31 is positioned at the measurement spot.

In a case where a series of measurement compliant with the measurement procedure associated by the measurement procedure association unit 39 is completed at the measurement spot of the subject S decided by the measurement spot decision unit 38, the navigation image generation unit 37 can include information representing that the series of measurement is completed at the measurement spot, in the navigation image. For example, though not shown, the navigation image generation unit 37 can include information representing that the series of measurement is completed, in the navigation image by coloring the measurement spot mark indicating the measurement spot where the series of measurement is completed, with a given color, in a case where the measurement spot mark is formed with one closed broken line, changing one close broken line to two closed broken lines, or disposing text data representing that the series of measurement is completed, near the measurement spot. With this, the user can clearly recognize the measurement spot where the series of measurement is completed, and can smoothly perform ultrasonography of the subject S.

Figure 16:
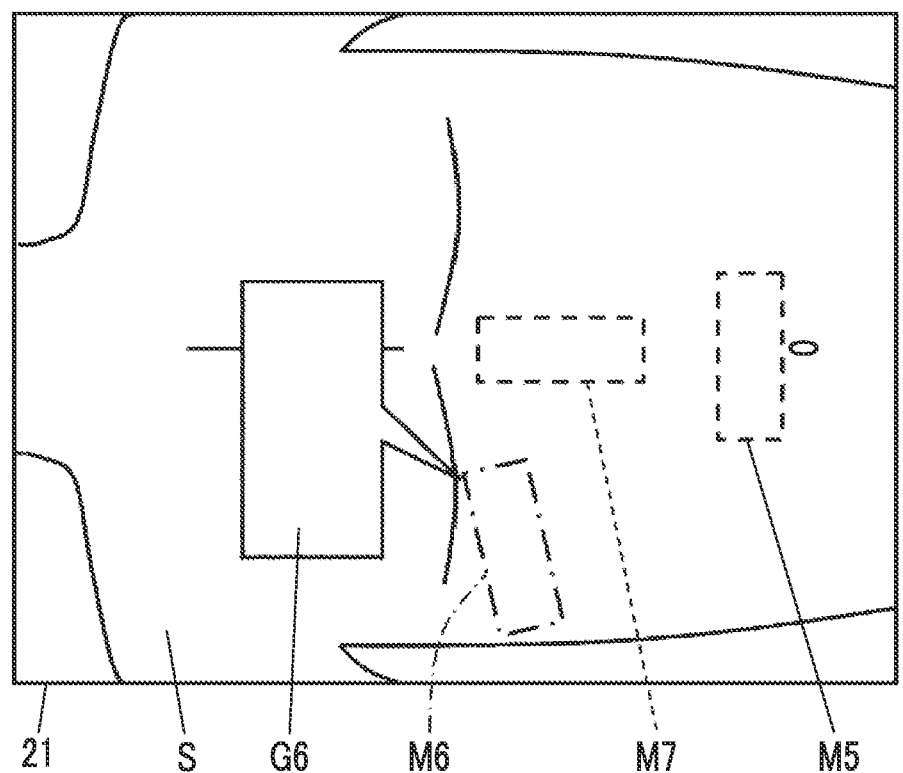
FIG. 16 is a diagram showing an example of a navigation image that includes a plurality of measurement spot marks of the subject in Embodiment 3 of the invention.

In a case where a plurality of measurement spots of the subject S are decided by the measurement spot decision unit 38, for example, as shown in FIG. 16, the navigation image generation unit 37 can generate a navigation image in which the measurement spot closest to the ultrasound probe 31 detected by the probe detection unit 62 among a plurality of measurement spots is highlighted. In the example shown in FIG. 16, the ultrasound probe 31 (not shown) is positioned at the measurement spot mark M6 indicating "right subcostal", and while the measurement spot mark M5 indicating "below solar plexus to navel" and the measurement spot mark M7 indicating "below solar plexus" are formed with a closed broken line, the measurement spot mark M6 is formed with a one-dot chain line. With this, the user can clearly recognize the measurement spot closest to the ultrasound probe 31 among a plurality of measurement spots.

In a case where a plurality of measurement spots of the subject S are decided by the measurement spot decision unit 38, for example, as shown in FIG. 16, the navigation image generation unit 37 can include only information representing the part in the subject S and the status of the part related to the measurement spot closest to the ultrasound probe 31 detected by the probe detection unit 62 among a plurality of measurement spots, information representing the measurement procedure, and information representing the description to be the ground for the decision of the measurement spot, in the navigation image. In the example shown in FIG. 16, the navigation image includes a corresponding guide panel G6 only for the measurement spot mark M6 indicating "right subcostal" as the measurement spot closest to the ultrasound probe 31 detected by the probe detection unit 62 among the three measurement spot marks M5 to M7, but does not include guide panels corresponding to other measurement spot marks M5 and M7. For this reason, the field of view in front is prevented from being obstructed by a plurality of guide panels corresponding to a plurality of measurement spots in the navigation image.

As described above, with the ultrasound diagnostic apparatus of Embodiment 3, the ultrasound probe 31 shown in the camera image is detected by the probe detection unit 62 of the diagnostic apparatus body 3A, and various kinds of guidance related to the measurement spot of the subject S decided by the measurement spot decision unit 38 are provided to the user based on the detected position of the ultrasound probe 31 during ultrasonography of the subject S. Therefore, it is possible to allow the user to easily perform ultrasonography of the subject S.

Embodiment 4

Although the ultrasound diagnostic apparatus 1 of Embodiment 1 has a configuration in which the head-mounted display 2 and the diagnostic apparatus body 3 are connected by wireless communication, and the ultrasound probe 31 and the input device 42 are connected directly to the body processor 45 in the diagnostic apparatus body 3, for example, the head-mounted display 2, the diagnostic apparatus body 3, the ultrasound probe 31, and the input device 42 can also be connected to each other indirectly through a network.

Figure 17:
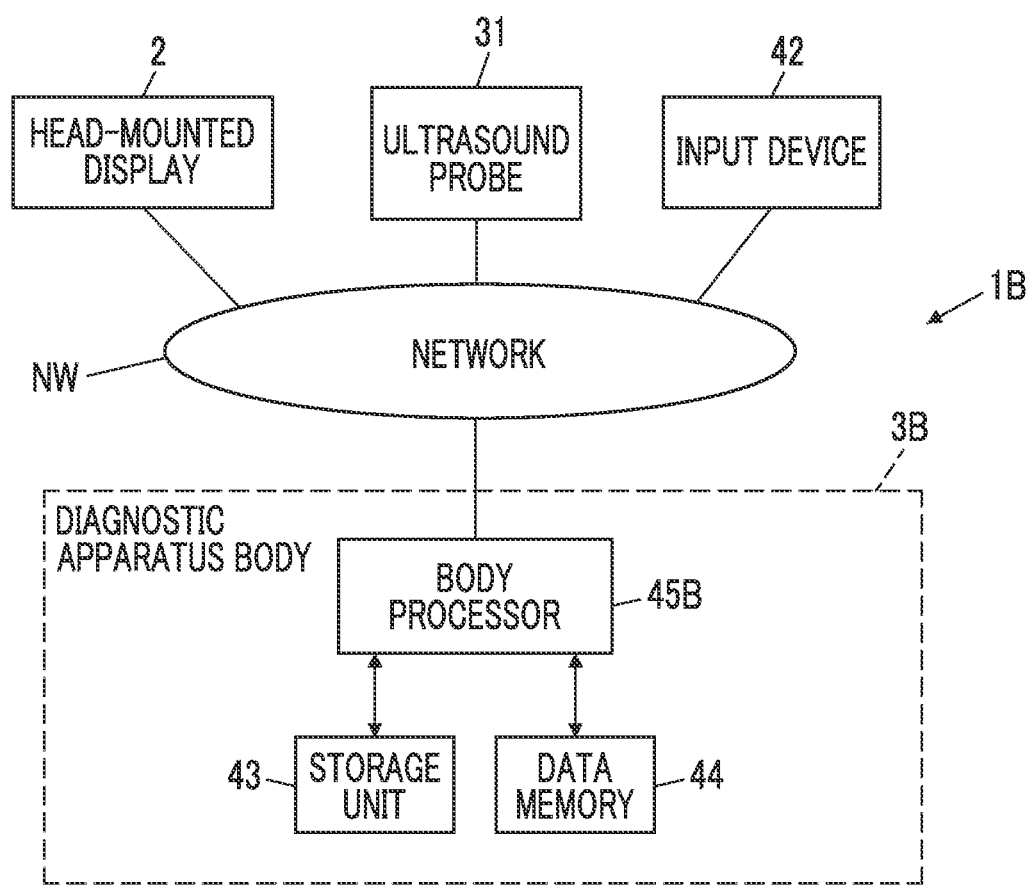
FIG. 17 is a block diagram showing the configuration of an ultrasound diagnostic apparatus according to Embodiment 4 of the invention.

As shown in FIG. 17, an ultrasound diagnostic apparatus 1B according to Embodiment 4 has a configuration in which the head-mounted display 2, the ultrasound probe 31, and the input device 42 are connected to a diagnostic apparatus body 3B through a network NW. The diagnostic apparatus body 3B has a configuration in which the ultrasound probe 31 and the input device 42 in the diagnostic apparatus body 3 in Embodiment 1 shown in FIG. 4 are removed, and is configured with the storage unit 43, the data memory 44, and a body processor 45B.

Even though the ultrasound diagnostic apparatus 1B has such a configuration, similarly to the ultrasound diagnostic apparatus 1 of Embodiment 1, the measurement spot of the subject S is automatically decided based on the subject information input by the user through the input device 42, and the decided measurement spot is displayed on the display unit 21 of the head-mounted display 2. Therefore, it is possible to allow the user to easily perform ultrasonography on the subject S regardless of user's proficiency.

The head-mounted display 2, the ultrasound probe 31, and the input device 42 are connected to the diagnostic apparatus body 3B through the network NW, and thus, the diagnostic apparatus body 3B can be used as a so-called remote server. With this, for example, the user can perform ultrasonography of the subject S by mounting the head-mounted display 2 on the head and preparing the ultrasound probe 31 and the input device 42 at hand, and thus, it is possible to improve convenience in performing ultrasonography.

Although the body processor 45B of the diagnostic apparatus body 3B comprises the transmission and reception unit 32, the transmission and reception controller 33, the ultrasound image generation unit 34, the navigation image generation unit 37, the measurement spot decision unit 38, the measurement procedure association unit 39, and the ground derivation unit 40, the body processor 45B may not comprise the transmission and reception unit 32, the transmission and reception controller 33, the ultrasound image generation unit 34, and the navigation image generation unit 37, the ultrasound probe 31 may comprise the transmission and reception unit 32, the transmission and reception controller 33, and the ultrasound image generation unit 34, and the head-mounted display 2 may comprise the navigation image generation unit 37. In this case, the measurement spot of the subject S is decided by the measurement spot decision unit 38 of the body processor 45B based on the subject information input by the user through the input device 42, and the navigation image indicating the measurement spot of the subject S is generated by the navigation image generation unit 37 of the head-mounted display 2 based on information representing the measurement spot of the subject S decided by the measurement spot decision unit 38 of the body processor 45B and the camera image acquired by the camera unit 22 of the head-mounted display 2.

For this reason, even in a case where the body processor 45B does not comprise the transmission and reception unit 32, the transmission and reception controller 33, the ultrasound image generation unit 34, and the navigation image generation unit 37, the ultrasound probe 31 comprises the transmission and reception unit 32, the transmission and reception controller 33, and the ultrasound image generation unit 34, and the head-mounted display 2 comprises the navigation image generation unit 37, similarly to a case where the body processor 45B comprises the transmission and reception unit 32, the transmission and reception controller 33, the ultrasound image generation unit 34, and the navigation image generation unit 37, the measurement spot of the subject S is automatically decided based on the subject information input by the user through the input device 42, and the decided measurement spot is displayed on the display unit 21 of the head-mounted display 2. Therefore, it is possible to allow the user to easily perform ultrasonography on the subject S regardless of user's proficiency.

Although application of the aspect of Embodiment 4 to Embodiment 1 has been described, the aspect of Embodiment 4 can be similarly applied to Embodiment 2 and Embodiment 3.

EXPLANATION OF REFERENCES 1, 1B: ultrasound diagnostic apparatus
2: head-mounted display
3, 3A, 3B: diagnostic apparatus body
21, 21A, 21B: display unit
22: camera unit
23: head-mounted display-side wireless communication unit 24, 36: communication controller
25: display controller
26: head-mounted display controller
27: head-mounted display processor
28: battery
31: ultrasound probe
31A: transducer array
32: transmission and reception unit
33: transmission and reception controller
34: ultrasound image generation unit
35: body-side wireless communication unit
37: navigation image generation unit
38: measurement spot decision unit
39: measurement procedure association unit
40: ground derivation unit
41, 41A: body controller
42: input device
43: storage unit
44: data memory
45, 45A, 45B: body processor
51: transmission unit
52: reception unit
53: amplification unit
54: AD conversion unit
56: B mode image generation unit
57: Doppler image generation unit
61: navigation information derivation unit
62: probe detection unit
63: position determination unit
64: part recognition unit
65: measurement unit,
A: temple portion
B: bridge portion
D: accommodation portion
G1, G2, G3, G4, G6: guide panel
F: imaging lens
M, M3, M4, M5, M6, M7: measurement spot mark
N1, N2, N3: number
NW: network
P: arrow
S: subject

What is claimed is:

1. An ultrasound diagnostic apparatus comprising:
an ultrasound probe that is positioned at a measurement spot of a subject to perform transmission and reception of an ultrasonic wave to and from the subject;
a head-mounted display that is mounted on a head of a user and has a camera unit configured to acquire a camera image obtained by imaging a field of view in front of the user and a display unit;
a processor configured to, in a case where subject information including a plurality of symptoms of the subject are input,
derive a plurality of candidates of the measurement spot based on the plurality of symptoms, where the plurality of candidates include at least one candidate related with only one of the plurality of symptoms and at least one candidate related with to two or more of the plurality of symptoms,
store in advance a predetermined threshold value having a value corresponding to two or more number of related symptoms in each of the plurality of candidates,
decide at least one measurement spot where the transmission and reception of the ultrasonic wave by the ultrasound probe is desired, by narrowing down the plurality of candidates to leave candidates where the number of related symptoms is equal to or greater than the predetermined threshold value,
recognize the subject from the camera image acquired by the camera unit of the head-mounted display,
generate a navigation image indicating a position of the decided measurement spot with respect to the recognized subject, and
display the generated navigation image on the display unit of the head-mounted display.

2. The ultrasound diagnostic apparatus according to claim 1,
wherein the subject information further includes at least one of a medical history, a status of treatment, a health status, or information regarding a body of the subject.

3. The ultrasound diagnostic apparatus according to claim 1,
wherein the processor is further configured to derive a plurality of parts in the subject related to the plurality of symptoms as the plurality of candidates, and statuses of the plurality of the parts from the subject information.

4. The ultrasound diagnostic apparatus according to claim 3,
wherein the processor includes information representing the part in the subject and the status of the part used for the decision of the measurement spot, in the navigation image.

5. The ultrasound diagnostic apparatus according to claim 3,
wherein the processor is further configured to
associate a given measurement procedure with the plurality of parts in the subject and the status of the plurality of parts,
include information representing the measurement procedure, in the navigation image.

6. The ultrasound diagnostic apparatus according to claim 1,
wherein the processor is further configured to
extract a keyword related to the measurement spot from the subject information,
derive a description to be a ground for the decision of the measurement spot based on the keyword, and
include information representing the description to be the ground, in the navigation image.

7. The ultrasound diagnostic apparatus according to claim 1,
wherein the processor is further configured to
detect the ultrasound probe from the camera image acquired by the camera unit of the head-mounted display, and
determine whether or not a position of the ultrasound probe overlaps the position of the measurement spot indicated by the navigation image.

8. The ultrasound diagnostic apparatus according to claim 7,
wherein the processor is further configured to
control the transmission and reception of the ultrasonic wave by the ultrasound probe in a given observation mode and under a given transmission and reception condition.

9. The ultrasound diagnostic apparatus according to claim 8,
wherein, in a case where it is determined that the position of the ultrasound probe overlaps the position of the measurement spot,
the processor is further configured to control the transmission and reception of the ultrasonic wave by the ultrasound probe under a transmission and reception condition corresponding to the measurement spot where the ultrasound probe is positioned.

10. The ultrasound diagnostic apparatus according to claim 8,
wherein, in a case where it is determined that the position of the ultrasound probe overlaps the position of the measurement spot,
the processor is further configured to control the transmission and reception of the ultrasonic wave by the ultrasound probe in an observation mode corresponding to the measurement spot where the ultrasound probe is positioned.

11. The ultrasound diagnostic apparatus according to claim 8,
wherein the processor is further configured to
generate an ultrasound image based on a reception signal acquired through the transmission and reception of the ultrasonic wave to and from the subject by the ultrasound probe,
in a case where it is determined that the position of the ultrasound probe overlaps the position of the measurement spot,
recognize a part in the subject from the ultrasound image, and
control the transmission and reception of the ultrasonic wave by the ultrasound probe under a transmission and reception condition corresponding to the part in the subject.

12. The ultrasound diagnostic apparatus according to claim 11,
wherein the processor is further configured to
in a case where the part in the subject is recognized, perform measurement regarding the part based on the ultrasound image under a measurement condition corresponding to the part in the subject.

13. The ultrasound diagnostic apparatus according to claim 7,
wherein, in a case where a plurality of the measurement spots are decided, the processor is further configured to generate the navigation image in which the measurement spot closest to the position of the ultrasound probe among the plurality of measurement spots is highlighted.

14. The ultrasound diagnostic apparatus according to claim 7,
wherein the processor is further configured to
estimate a plurality of parts in the subject and statuses of the plurality of parts based on the subject information, and decides a plurality of the measurement spots based on the plurality of estimated parts in the subject and the estimated statuses of the plurality of parts, and
include only information representing the part in the subject related to the measurement spot closest to the position of the ultrasound probe and the status of the part among the parts in the subject related to the plurality of measurement spots and the statuses of the parts, in the navigation image.

15. The ultrasound diagnostic apparatus according to claim 5,
wherein the processor is further configured to
detect the ultrasound probe from the camera image captured by the camera unit of the head-mounted display,
determine whether or not a position of the ultrasound probe overlaps the position of the measurement spot indicated by the navigation image, and
control the transmission and reception of the ultrasonic wave by the ultrasound probe in a given observation mode and under a given transmission and reception condition,
in a case where the processor determines that the position of the ultrasound probe overlaps the position of the measurement spot,
control the transmission and reception of the ultrasonic wave by the ultrasound probe in an observation mode and under a transmission and reception condition based on the measurement procedure associated with the part in the subject related to the measurement spot where the ultrasound probe is positioned and the status of the part.

16. The ultrasound diagnostic apparatus according to claim 1,
wherein the processor is further configured to
estimate a plurality of parts in the subject and statuses of the plurality of parts based on the subject information,
decide the measurement spot based on the plurality of estimated parts in the subject and the estimated statuses of the plurality of parts,
store a given degree of urgency with respect to each of a plurality of estimable parts in the subject and statuses of the plurality of parts, and
include information representing the degree of urgency of a part in the subject and a status of the part related to the measurement spot, in the navigation image.

17. The ultrasound diagnostic apparatus according to claim 16,
wherein the processor is further configured to
decide a plurality of the measurement spots based on the plurality of estimated parts in the subject and the estimated statuses of the plurality of parts,
give priority to the plurality of measurement spots based on the degree of urgency of the plurality of estimated parts in the subject, and
generate the navigation image with the plurality of measurement spots given the priority.

18. The ultrasound diagnostic apparatus according to claim 1, further comprising:
an input device that is provided for the user to perform an input operation,
wherein the subject information is input by the user through the input device.

19. A method of controlling an ultrasound diagnostic apparatus, the method comprising:
acquiring a camera image obtained by imaging a subject with a camera unit of a head-mounted display mounted on a head of a user;
in a case where subject information including a plurality of symptoms of the subject are input,
deriving a plurality of candidates of a measurement spot based on the plurality of symptoms, where the plurality of candidates include at least one candidate related with only one of the plurality of symptoms and at least one candidate related with two or more of the plurality of symptoms;
storing in advance a predetermined threshold value having a value corresponding to two or more number of related symptoms in each of the plurality of candidates;
deciding a measurement spot where transmission and reception of an ultrasonic wave by an ultrasound probe is desired, by narrowing down the plurality of candidates to leave candidates where the number of related symptoms is equal to or greater than the predetermined threshold value;

recognizing the subject from the acquired camera image and generating a navigation image indicating a position of the measurement spot with respect to the recognized subject; and displaying the generated navigation image on a display unit of the head-mounted display.

* * * * *